United States Patent
Kato et al.

(10) Patent No.: US 11,872,327 B2
(45) Date of Patent: Jan. 16, 2024

(54) MEDICAL DEVICE

(71) Applicant: Toray Industries, Inc., Tokyo (JP)

(72) Inventors: Tomohiro Kato, Otsu (JP); Masataka Nakamura, Otsu (JP)

(73) Assignee: Toray Industries, Inc., Tokyo (JP)

( * ) Notice: Subject to any disclaimer, the term of this patent is extended or adjusted under 35 U.S.C. 154(b) by 893 days.

(21) Appl. No.: 16/611,078

(22) PCT Filed: Apr. 19, 2018

(86) PCT No.: PCT/JP2018/016155
§ 371 (c)(1),
(2) Date: Nov. 5, 2019

(87) PCT Pub. No.: WO2018/207586
PCT Pub. Date: Nov. 15, 2018

(65) Prior Publication Data
US 2020/0164112 A1    May 28, 2020

(30) Foreign Application Priority Data
May 10, 2017 (JP) ................................ 2017-093709

(51) Int. Cl.
*A61L 29/14* (2006.01)
*A61L 15/26* (2006.01)
*A61L 15/60* (2006.01)
*A61L 27/18* (2006.01)
*A61L 27/52* (2006.01)
*A61L 29/06* (2006.01)
*A61L 31/06* (2006.01)
*A61L 31/14* (2006.01)
*C08G 77/442* (2006.01)
*G02B 1/04* (2006.01)

(52) U.S. Cl.
CPC ............ *A61L 29/145* (2013.01); *A61L 15/26* (2013.01); *A61L 15/60* (2013.01); *A61L 27/18* (2013.01); *A61L 27/52* (2013.01); *A61L 29/06* (2013.01); *A61L 31/06* (2013.01); *A61L 31/145* (2013.01); *C08G 77/442* (2013.01); *G02B 1/043* (2013.01); *C08G 2220/00* (2013.01)

(58) Field of Classification Search
CPC .. G02B 1/043; C08G 2220/00; C08G 77/442; A61L 29/145; A61L 15/26; A61L 15/60; A61L 27/18; A61L 27/52; A61L 29/06; A61L 31/06; A61L 31/145
See application file for complete search history.

(56) References Cited

U.S. PATENT DOCUMENTS

| | | | |
|---|---|---|---|
| 4,423,195 A * | 12/1983 | Covington | ............... B29C 33/52 |
| | | | 528/26 |
| 4,463,149 A | 7/1984 | Ellis | |
| 9,034,942 B2 | 5/2015 | Baba et al. | |
| 9,057,822 B2 | 6/2015 | Liu et al. | |
| 9,588,258 B2 | 3/2017 | Alli et al. | |
| 9,981,434 B2 | 5/2018 | Alli et al. | |
| 2004/0014898 A1 | 1/2004 | Ichihara | |
| 2012/0220689 A1 * | 8/2012 | Yao | ......................... G02B 1/043 |
| | | | 53/425 |
| 2013/0341811 A1 | 12/2013 | Alli et al. | |
| 2015/0274854 A1 | 10/2015 | Tamiya et al. | |
| 2017/0198077 A1 * | 7/2017 | Ito | ......................... C08F 290/06 |
| 2017/0204213 A1 | 7/2017 | Kato et al. | |

FOREIGN PATENT DOCUMENTS

| | | |
|---|---|---|
| EP | 2745854 A1 | 6/2014 |
| EP | 3162824 A1 | 5/2017 |
| JP | 58169127 A | 10/1983 |
| JP | 2001188101 A | 7/2001 |
| JP | 2004037811 A | 2/2004 |
| JP | 2011219512 A | 11/2011 |
| JP | 2011219513 A | 11/2011 |
| JP | 2014040598 A | 3/2014 |
| JP | 2014510945 A | 5/2014 |
| JP | 2014512561 A | 5/2014 |
| JP | 2015504108 A | 2/2015 |
| JP | 2015524089 A | 8/2015 |
| JP | 2015524090 A | 8/2015 |
| WO | 2015153403 A1 | 10/2015 |
| WO | 2015198919 A1 | 12/2015 |
| WO | WO-2015186634 A1 * | 12/2015 ....... B29D 11/00134 |

OTHER PUBLICATIONS

MCR-M11 (Year: 2014).*
MCR-M07 (Year: 2014).*

(Continued)

*Primary Examiner* — Sean M Basquill
(74) *Attorney, Agent, or Firm* — RatnerPrestia

(57) ABSTRACT

A medical device including a silicone hydrogel which is less likely to harden due to drying, and which is less likely to cause stimulation at a site in contact with a human body, is disclosed. The medical device includes a silicone hydrogel satisfying the following conditions: (1) the water content in hydrous state is within the range of 10% by mass to 70% by mass; (2) the content of silicon atoms with respect to the total mass in dry state is within the range of 8% by mass to 30% by mass; and (3) the tensile elastic modulus in dry state is within the range of 0.1 MPa to 3.5 MPa.

9 Claims, No Drawings

(56) References Cited

OTHER PUBLICATIONS

I. Tranoudis & Nathan Efron, Tensile Properties of Soft Contact Lens Materials, 27 Con. Lens Ant. Eye 177 (Year: 2004).*
Karen French, Contact Lens Material Properties Part 2—Mechanical Behaviour and Modulus, 230 Optician 29 (Year: 2005).*
Michel Guillon, Are Silicone Hydrogel Contact Lenses More Comfortable than Hydrogel Contact Lenses, 39 Eye Con. Lens 86 (Year: 2013).*
Extended European Search Report for European Application No. 18 799 317.5, dated Dec. 7, 2020, 8 pages.
International Search Report and Written Opinion for International Application No. PCT/JP2018/016155, dated Jun. 12, 2018, 9 pages.

* cited by examiner

MEDICAL DEVICE

CROSS REFERENCE TO RELATED APPLICATIONS

This is the U.S. National Phase application of PCT/JP2018/016155, filed Apr. 19, 2018, which claims priority to Japanese Patent Application No. 2017-093709, filed May 10, 2017, the disclosures of these applications being incorporated herein by reference in their entireties for all purposes.

FIELD OF THE INVENTION

The present invention relates to a medical device, especially to a medical device using a silicone hydrogel.

BACKGROUND OF THE INVENTION

Medical devices to be in direct contact with part of the human body are well known, and flexible materials that are less likely to injure the human body are required therefor. In particular, for medical devices to be in contact with wet sites such as mucosae, hydrous materials having excellent flexibility such as hydrogels are suitable. Examples of such medical devices include ophthalmic lenses, endoscopes, and catheters. All of these are medical devices to be in contact with wet sites such as mucosae, and examples of modes of ophthalmic lenses include soft contact lenses.

As materials of soft contact lenses, silicone hydrogels are known. A silicone hydrogel is obtained by combination of at least one silicone component and at least one hydrophilic component.

For example, Patent Documents 1 to 8 disclose methods of producing silicone hydrogels that can be used for ophthalmic lenses.

On the other hand, users of contact lenses often experience discomfort associated with a feeling of dryness when they use the lenses. Such discomfort may lead to deterioration of health of the eyes, and, in serious cases, it may cause symptoms such as dry eye. Therefore, development of a contact lens material with which the discomfort associated with a feeling of dryness is suppressed, and which is less likely to deteriorate health of the eyes, has been demanded.

Further, for contact lenses that are less likely to deteriorate health of the eyes, it is important to have sufficient surface wettability and oxygen permeability, and to have a surface resistant to adhesion of body-derived fouling such as proteins and lipids.

Accordingly, the contact lenses require a material satisfying these properties in a well-balanced manner.

PATENT DOCUMENTS

[Patent Document 1] JP 58-169127 A
[Patent Document 2] JP 2004-37811 A
[Patent Document 3] JP 2011-219512 A
[Patent Document 4] JP 2011-219513 A
[Patent Document 5] JP 2014-40598 A
[Patent Document 6] JP 2015-524089 A
[Patent Document 7] JP 2015-524090 A
[Patent Document 8] WO 2015/198919

SUMMARY OF THE INVENTION

For medical devices to be in contact with part of the human body, it is important to suppress hardening due to drying. However, in general, hydrogel materials often become hard and fragile due to drying. Further, medical devices lose their flexibility with time especially when they are in contact with moving parts of the human body such as an eyeball or skin for a long time. Such devices are therefore not suitable for long-term use, which is problematic.

Examples of the above problems include discomfort due to a feeling of dryness caused by contact lenses. One cause of the feeling of dryness or discomfort caused by contact lenses is stimulation of the eyeball due to hardening of a lens material which is becoming dry. In general, most hydrophilic monomers used for formation of silicone hydrogels have polar groups, and therefore have strong interactions. Thus, they tend to show hardening caused by aggregation of polymer chains due to dehydration of the gels. When the hardening occurs due to the drying, stimulation of the human body occurs at a contact site. This may lead to adverse effects such as damaging of a contact site such as a mucosa.

Patent Document 1 describes a method of producing a hard contact lens using a branched silicone monomer. However, since a material with such a composition is less likely to contain water, and is hard, it gives a poor comfort. Further, since it has a surface with strong hydrophobicity, adsorption of body-derived molecules to the surface tends to occur, which is problematic.

Patent Documents 2 to 5 describe methods of producing a contact lens using a silicone hydrogel. However, the methods have an industrially disadvantageous aspect because of requirement of preparation of a silicone macromonomer containing a urethane bond. Further, because of use of a branched silicone monomer, the lens shows poor shape recovery performance. For example, in cases where a large amount of a hydrophilic monomer such as N-vinyl pyrrolidone is contained, the lens shows a relatively high tensile elastic modulus even in hydrous state, so that hardening occurs in some cases due to drying, causing stimulation of the eyeball.

Patent Documents 6 and 7 describe methods of producing a contact lens using a silicone hydrogel. However, since the lens contains a hydrophilic polymer such as polyvinyl pyrrolidone as an internal wetting agent, the lens easily becomes cloudy, so that balancing of the composition is difficult in some cases. Further, since the lens has a relatively high tensile elastic modulus even in hydrous state, hardening occurs in some cases due to drying, causing stimulation of the eyeball.

Patent Document 8 describes a method of obtaining a silicone hydrogel having uniform mechanical properties by using monomers having the same polymerizable functional group in copolymerization. However, because of use of a branched silicone monomer, the lens shows poor shape recovery performance. Moreover, although the lens has an excellent transparency due to strong interactions between functional groups, it has a decreased water content, resulting in a relatively high tensile elastic modulus even in hydrous state. Therefore, hardening occurs in some cases due to drying, causing stimulation of the eyeball.

In general, hardening due to drying can be easily suppressed by decreasing water content. However, low water content leads to decreased wettability, that is, decreased biocompatibility, which is not preferred. On the other hand, high water content allows achievement of excellent wettability, but leads to low oxygen permeability, which is not preferred. For balancing between oxygen permeability and water content, compatibility between silicone monomers and hydrophilic monomers is important.

However, in cases where interactions between monomers are used to obtain the compatibility, transparency and shape recovery performance are deteriorated in some cases, so that the control may be difficult. It may thus be difficult to obtain a material satisfying these desired physical properties in a well-balanced manner.

In view of the facts described above, it is of great significance to develop a silicone hydrogel having an appropriate tensile elastic modulus in hydrous state, and having an excellent transparency and shape recovery performance, the silicone hydrogel being a material which is less likely to harden due to drying, and which is therefore less likely to stimulate the eyeball.

Furthermore, in cases where such a material, which is less likely to stimulate the eyeball, has excellent oxygen permeability and higher resistance to adhesion of body-derived molecules such as proteins and lipids, eye health is not deteriorated, which is preferred. Furthermore, in cases where such a material can be obtained without special and laborious production of macromonomers, an industrial advantage can be obtained, which is more preferred.

Such a material is suitable as ophthalmic lenses, and moreover, can be suitably used as a variety of medical devices represented by endoscopes, catheters, infusion tubes, gas transfer tubes, stents, sheaths, cuffs, tube connectors, access ports, drainage bags, blood circuits, wound dressings, and drug carriers.

In view of this, an object of the present invention is to provide a medical device containing a silicone hydrogel which is less likely to harden due to drying, and which is less likely to cause stimulation at a site in contact with a human body.

As a result of intensive study to achieve the above object, the present inventors discovered that a medical device containing a silicone hydrogel having the following constitution is useful.

[1] A medical device comprising a silicone hydrogel satisfying the following conditions:
  (1) the water content in hydrous state is within the range of 10% by mass to 70% by mass;
  (2) the content of silicon atoms with respect to the total mass in dry state is within the range of 8% by mass to 30% by mass; and
  (3) the tensile elastic modulus in dry state is within the range of 0.1 MPa to 3.5 MPa.

[2] The medical device according to [1], wherein the tensile elastic modulus is within the range of 0.1 MPa to 1.5 MPa.

[3] The medical device according to [1] or [2], comprising a silicone hydrogel having a dry elastic modulus ratio of 1 to 10, wherein the dry elastic modulus ratio is represented by the following Equation 1:

dry elastic modulus ratio=the tensile elastic modulus in dry state/tensile elastic modulus in hydrous state. (1)

[4] The medical device according to any one of [1] to [3], wherein the silicone hydrogel has a zero-stress period of 0.1 second to 2 seconds in hydrous state,
  wherein the zero-stress period means a length of time during tensile stress measurement in which an operation of
    drawing a test piece having a width of 5 mm and a thickness within the range of 0.05 mm to 0.2 mm held at an inter-supporting-point distance of 5 mm, using a load cell with a maximum load of 2 kg at a rate of 100 mm/minute, until the inter-supporting-point distance becomes 10 mm, and then
    reducing the inter-supporting-point distance to 5 mm at the same rate, is repeated three times while obtaining measured values at 20-millisecond intervals,
  the length of time being a length of time
    from the time point when the stress becomes zero during the second reduction of the inter-supporting-point distance to 5 mm
    to the time point when the stress becomes non-zero after starting the third drawing, wherein zero stress means a state with a measured value within the range of −0.05 gf to 0.05 gf.

[5] The medical device according to any one of [1] to [4], wherein the silicone hydrogel has a tensile elongation at break within the range of 200% to 1000% in hydrous state.

[6] The medical device according to any one of [1] to [5], wherein the silicone hydrogel has a tensile elastic modulus within the range of 0.1 MPa to 1.5 MPa in hydrous state.

[7] The medical device according to any one of [1] to [6], wherein the silicone hydrogel comprises a repeat unit (A) derived from a monomer represented by General Formula (I):

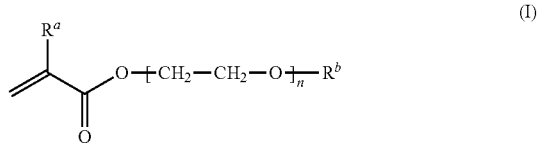

wherein, in General Formula (I), $R^a$ represents hydrogen or a methyl group; $R^b$ represents a hydrogen atom, a sulfonic group, a phosphate group, or an organic group having from 1 to 15 carbon atoms; and n represents an integer within the range of 1 to 40.

[8] The medical device according to [7], comprising the repeat unit (A) derived from a monomer represented by General Formula (I) in an amount within the range of 5% by mass to 50% by mass with respect to the total mass of the silicone hydrogel in dry state.

[9] The medical device according to any one of [1] to [8], wherein the silicone hydrogel contains a repeat unit (B) derived from a monofunctional linear silicone monomer.

[10] The medical device according to [9], comprising the repeat unit (B) derived from a monofunctional linear silicone monomer in an amount within the range of 20% by mass to 70% by mass with respect to the total mass of the silicone hydrogel in dry state.

[11] The medical device according to any one of [1] to [10], wherein the silicone hydrogel contains a repeat unit (C) derived from a monomer containing an amide structure.

[12] The medical device according to [11], comprising the repeat unit (C) derived from a monomer containing an amide structure, in an amount within the range of 5% by mass to 50% by mass with respect to the total mass of the silicone hydrogel in dry state.

[13] The medical device according to [11] or [12], wherein at least one of the repeat unit (A) derived from a monomer represented by General Formula (I) and the repeat unit (C) derived from a monomer containing an amide structure has a glass transition temperature of not more than 20° C. in a state of a homopolymer.

[14] The medical device according to any one of [1] to [13], which is any one selected from the group consisting of ophthalmic lenses, endoscopes, catheters, infusion tubes, gas transfer tubes, stents, sheaths, cuffs, tube connectors, access ports, drainage bags, blood circuits, wound dressings, and drug carriers.

[15] The medical device according to any one of [1] to [14], which is a contact lens.

[16] The medical device according to any one of [1] to [15], wherein the silicone hydrogel is a polymer comprising:

a repeat unit (A) derived from a monomer represented by General Formula (I):

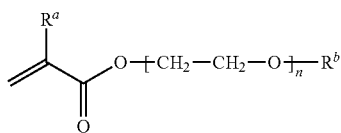

wherein, in General Formula (I), $R^a$ represents hydrogen or a methyl group; $R^b$ represents a hydrogen atom, a sulfonic group, a phosphate group, or an organic group having from 1 to 15 carbon atoms; and n represents an integer within the range of 1 to 40;

a repeat unit (B) derived from a monomer represented by General Formula (a):

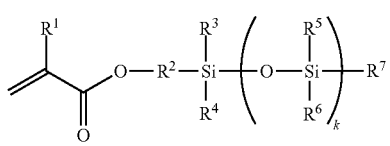

wherein, in General Formula (a), $R^1$ represents a hydrogen atom or a methyl group; $R^2$ represents a divalent $C_1$-$C_{20}$ organic group; $R^3$ to $R^6$ each independently represent a $C_1$-$C_{20}$ alkyl group which is optionally substituted, or a $C_6$-$C_{20}$ aryl group which is optionally substituted; $R^7$ represents a $C_1$-$C_{20}$ alkyl group or a $C_6$-$C_{20}$ aryl group; and k represents an integer of 1 to 200 which optionally has a distribution; and a repeat unit (C) derived from a monomer represented by General Formula (II-1):

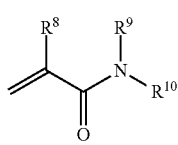

or General Formula (II-2):

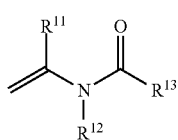

wherein, in General Formula (II-1) and General Formula (II-2), $R^8$ and $R^{11}$ each independently represent a hydrogen atom or a methyl group; $R^9$ and $R^{10}$, and $R^{12}$ and $R^{13}$ represent a hydrogen atom(s), and/or a $C_1$-$C_{20}$ alkyl group(s) which is/are either branched or linear, which optionally contain(s) a cyclic structure, and which is/are optionally substituted; and $R^{12}$ and $R^{13}$ optionally bind to each other to form a ring.

[17] The medical device according to [16], comprising:
the repeat unit (A) in an amount within the range of 5% by mass to 50% by mass with respect to the total mass of the silicone hydrogel in dry state;
the repeat unit (B) in an amount within the range of 20% by mass to 70% by mass with respect to the total mass of the silicone hydrogel in dry state; and
the repeat unit (C) in an amount within the range of 5% by mass to 50% by mass with respect to the total mass of the silicone hydrogel in dry state; with the proviso that the total of the repeat units (A), (B), and (C) does not exceed 100% by mass with respect to the total mass of the silicone hydrogel in dry state.

[18] The medical device according to [17], wherein the total of the repeat units (A), (B), and (C) exceeds 50% by mass with respect to the total mass of the silicone hydrogel in dry state.

By the present invention, a medical device containing a silicone hydrogel which is less likely to harden due to drying, and which is less likely to stimulate the human body especially at wet sites such as mucosae, can be obtained.

DETAILED DESCRIPTION OF EMBODIMENTS OF THE INVENTION

In the present invention, the hydrous state means a state after immersion of a silicone hydrogel in borate buffer at room temperature (25° C.) for not less than 24 hours. For measurement of physical properties in the hydrous state, a test piece is taken out of borate buffer, and, within 10 seconds thereafter, the borate buffer on the surface is lightly wiped off with a clean cloth at room temperature of 20° C. and a humidity of 50%, followed by performing the measurement at room temperature of 20° C. and a humidity of 50% within 1 minute thereafter.

The dry state in the present invention means a state after a silicone hydrogel in hydrous state is dried in a vacuum dryer at 40° C. for not less than 16 hours.

Measurement of physical properties in the dry state is carried out at room temperature of 20° C. and a humidity of 50% within 5 minutes after taking out a test piece of the dryer.

The water content in the present invention means the value obtained by measuring the mass of a silicone hydrogel in hydrous state (W1) and the mass of the silicone hydrogel in dry state (W2), and performing calculation according to the following equation.

Water content (%)=(W1−W2)/W1×100

The silicone hydrogel used in the present invention has a water content within the range of 10% by mass to 70% by mass in hydrous state. In cases where the water content is not less than 10% by mass, the biocompatibility is less likely to be poor. In cases where the water content is not less than 20% by mass, adsorption of proteins and lipids is less likely to occur, and therefore the contact lens is less likely to stick to the cornea. Accordingly, eye health is less likely to be adversely affected. On the other hand, in cases where the water content is not more than 70% by mass, oxygen permeability is less likely to be poor. In cases where the water content is not more than 50% by mass, shape change due to drying is small, so that stimulation of part of the human body such as the eyeball is less likely to occur. The lower limit is preferably 10% by mass, more preferably 20% by mass, still more preferably 25% by mass, still more preferably 30% by mass. The upper limit is preferably 70% by mass, more preferably 60% by mass, still more preferably 50% by mass, still more preferably 45% by mass. Any combination of the upper limit and the lower limit may be employed.

In the present invention, the content of silicon atoms with respect to the total mass of the silicone hydrogel in dry state means the value calculated according to the following equation:

Content of silicon atoms with respect to total mass of silicone hydrogel in dry state (%)=$\Sigma\{Si_m \times C_m\} \times 100$ Here, $Si_m$ represents the mass ratio of silicon atoms to the molecular weight of the silicone monomer used for the formation of the silicone hydrogel. $C_m$ represents the mass ratio of the silicone monomer to the dry mass of the silicone hydrogel. In cases where a plurality of silicone monomers are present, $Si_m$ is calculated for each component, and then multiplied by $C_m$, followed by calculating the total sum. In the present description, the content of silicon atoms with respect to the total mass of the silicone hydrogel in dry state may be referred to as the silicon atom content in dry state.

A description is given below for an example using a silicone hydrogel obtained by polymerization of a monomer composition composed of 25% by mass 3-[tris(trimethylsiloxy)silyl]propyl methacrylate (abbreviation: TRIS), 24% by mass 3-(trimethoxysilyl)propyl methacrylate (abbreviation: TMSM), 49% by mass N,N-dimethylacrylamide, and 2% by mass ethylene glycol dimethacrylate. Regarding TRIS, it has four silicon atoms for a molecular weight of 422.82. Therefore, when the mass of a silicon atom is regarded as 28.09 (g/mol), the calculation can be performed as follows: $Si_{m,TRIS}=28.09 \times 4/422.82 \approx 10.266$. Regarding TMSM, it has one silicon atom for a molecular weight of 248.35. Therefore, the calculation can be performed as follows: $Si_{m,TMSM}=28.09 \times 1/248.35$ 0.113. Accordingly, the content of silicon atoms in the silicone hydrogel (%) can be calculated as $(0.266 \times 0.25 + 0.113 \times 0.24) \times 100 = 9.842$.

The content of silicon atoms with respect to the total mass of the silicone hydrogel in dry state can be measured by ICP emission spectrochemical analysis. More specifically, the measurement is carried out according to the following procedure. A sample is washed with reverse osmosis water to remove salt and dirt, and then the sample, in dry state (4 to 5 mg), is weighed and taken in a platinum crucible. Sulfuric acid is then added thereto, followed by ashing of the sample by heating using a hot plate and a burner. The ashed product is melted with sodium carbonate, and then water is added thereto, followed by dissolving the product under heat, adding nitric acid thereto, and then adding water thereto to a constant volume. The resulting solution is subjected to measurement of the amount of Si element by ICP emission spectrochemical analysis, to determine the content in the sample.

In the silicone hydrogel used in the present invention, the content of silicon atoms with respect to the total mass of the silicone hydrogel in dry state is within the range of 8% by mass to 30% by mass. In cases where the content is not less than 8% by mass, the oxygen permeability is less likely to be insufficient. In cases where the content is not more than 30% by mass, the biocompatibility is less likely to be deteriorated as a result of low wettability due to high hydrophobicity. Further, the tensile elastic modulus is less likely to be high, and hardening is less likely to occur. The lower limit is preferably 8% by mass, more preferably 10% by mass, still more preferably 12% by mass, still more preferably 15% by mass. The upper limit is preferably 30% by mass, more preferably 28% by mass, still more preferably 25% by mass, still more preferably 22% by mass. Any combination of the upper limit and the lower limit may be employed.

From the viewpoint of preventing deterioration of eye health, the silicone hydrogel used in the present invention preferably has an oxygen permeability coefficient of not less than $30 \times 10^{-11}$ ($cm^2$/second) mL $O_2$/(mL·hPa), preferably has an oxygen permeability coefficient of not less than $40 \times 10^{-11}$ ($cm^2$/second) mL $O_2$/(mL·hPa), more preferably not less than $50 \times 10^{-11}$ ($cm^2$/second) mL $O_2$/(mL·hPa). The oxygen permeability coefficient is still more preferably not less than $70 \times 10^{-11}$ ($cm^2$/second) mL $O_2$/(mL·hPa), still more preferably not less than $90 \times 10^{-11}$ ($cm^2$/second) mL $O_2$/(mL·hPa). A silicone hydrogel having such an oxygen permeability can also be suitably used as a medical device such as a wound dressing since gas exchange on the skin and the like is not prevented. Although the upper limit of the oxygen permeability coefficient is not limited, the upper limit is realistically about $200 \times 10^{-11}$ ($cm^2$/second) mL $O_2$/(mL·hPa). The upper limit is more practically about $150 \times 10^{-11}$ ($cm^2$/second) mL $O_2$/(mL·hPa).

The oxygen permeability coefficient of the silicone hydrogel used in the present invention is a value measured by a film oxygen permeability meter based on the electrode method.

In the present invention, the wettability means the length of the surface liquid film retention time. It is important for the silicone hydrogel used in the present invention to have an excellent wettability of the surface from the viewpoint of biocompatibility. The surface liquid film retention time of the silicone hydrogel is preferably long. Here, the liquid film retention time is the length of time for which, when a silicone hydrogel immersed in borate buffer is taken out of the buffer and held in air such that the surface (in cases of an ophthalmic lens, the diameter direction) is vertically oriented, the liquid film on the surface of the silicone hydrogel is retained without being broken. The liquid film retention time is preferably not less than 10 seconds, more preferably not less than 15 seconds, still more preferably not less than 20 seconds, still more preferably not less than 30 seconds. The diameter herein means the diameter of the circle constituted by the edge portion of the ophthalmic lens. The liquid film retention time is measured using a sample in a wet state, that is, in hydrous state, prepared with borate buffer. Although the upper limit of the liquid film retention time is not limited, a realistic upper limit is about 100 seconds.

Since the silicone hydrogel used in the present invention is suitable for application to ophthalmic lenses, the silicone hydrogel used in the present invention preferably has a diameter of 6 mm to 25 mm. In particular, in cases of use as a soft contact lens, the silicone hydrogel more preferably has a spherical crown shape having a diameter of 10 mm to 17 mm, still more preferably has a spherical crown shape having a diameter of 13 mm to 15 mm. The lower limit is preferably 6 mm, more preferably 10 mm, still more preferably 13 mm. The upper limit is preferably 25 mm, more preferably 17 mm, still more preferably 15 mm. Any combination of the upper limit and the lower limit may be employed.

The silicone hydrogel used in the present invention has a tensile elastic modulus within the range of 0.1 MPa to 3.5 MPa in dry state. When the tensile elastic modulus in dry state is not less than 0.1 MPa, a sufficient followability is likely to be obtained, and, in cases of a contact lens, its spherical crown shape is likely to be maintained. When the tensile elastic modulus in dry state is not more than 3.5 MPa, stimulation of part of the human body such as the eyeball is less likely to be caused by dryness, so that deterioration of the comfort, or damaging, is less likely to be caused. The lower limit is preferably 0.35 MPa, more preferably 0.4 MPa, still more preferably 0.55 MPa, still more preferably 0.7 MPa, also preferably 0.8 MPa. The upper limit is preferably 3.5 MPa, more preferably 2.8 MPa, still more preferably 2.4 MPa, still more preferably 2 MPa, still more preferably 1.7 MPa, still more preferably 1.5 MPa. Any combination of the upper limit and the lower limit may be employed.

The tensile elastic modulus in dry state can be measured in dry state at room temperature of 20° C. and a humidity of 50% using a tensile tester such as Tensilon, within 5 minutes after taking out of a dryer.

The silicone hydrogel used in the present invention preferably has an excellent shape recovery performance. The shape recovery performance in the present invention means the time required for recovery to the original shape after giving certain deformation to a silicone hydrogel. Quicker recovery to the original shape indicates a better shape recovery performance, while slower recovery to the original shape indicates a poorer shape recovery performance. A material showing a poor shape recovery performance, especially when it is used as a soft contact lens, may cause delay of shape recovery of the lens after undergoing deformation by friction with the eyelid during blinking, resulting in deterioration of the comfort. The shape recovery performance in the present invention can be evaluated by measuring the zero-stress period of the silicone hydrogel in hydrous state.

The zero-stress period in hydrous state in the present invention means a length of time during tensile stress measurement wherein an operation in which a test piece of silicone hydrogel in hydrous state having a width of 5 mm and a thickness within the range of 0.05 mm to 0.2 mm held at an inter-supporting-point distance of 5 mm (State A) is drawn using a load cell with a maximum load of 2 kg at a rate of 100 mm/minute until the inter-supporting-point distance becomes 10 mm, and then the inter-supporting-point distance is reduced to 5 mm at the same rate, is repeated three times while obtaining measured values at 20-millisecond intervals, the length of time being a length of time from the time point when the stress becomes zero during the second reduction of the inter-supporting-point distance to 5 mm to the time point when the stress becomes non-zero after starting the third drawing, wherein zero stress means a state with a measured value within the range of −0.05 gf to 0.05 gf.

In State A, the test piece is held such that loosening of the test piece is avoided as much as possible, and such that the stress becomes zero.

The silicone hydrogel used in the present invention preferably has a zero-stress period within the range of 0.1 second to 2 seconds in hydrous state. In cases where the zero-stress period is not less than 0.1 second, the flexibility is not poor. In cases where the zero-stress period is not more than 2 seconds, the shape recovery performance is not poor, and, especially in the case of a contact lens, discomfort during use is not caused thereby. The lower limit is preferably 0.1 second, more preferably 0.2 second, still more preferably 0.5 second, still more preferably 0.7 second. The upper limit is preferably 2 seconds, more preferably 1.8 seconds, still more preferably 1.6 seconds, still more preferably 1.5 seconds, especially preferably 1.0 second. Any combination of the upper limit and the lower limit may be employed.

The zero-stress period in hydrous state can be obtained by taking out a test piece of borate buffer, and, within 10 seconds thereafter, lightly wiping off the borate buffer from the surface with a clean cloth at room temperature of 20° C. and a humidity of 50%, followed, within 1 minute thereafter, by placing the test piece in a mechanical property tester such as a Rheo Meter (product name; Sun Scientific Co., Ltd.) and performing measurement at room temperature of 20° C. and a humidity of 50%.

The silicone hydrogel used in the present invention is suitable for use as an ophthalmic lens among medical devices. In this case, the spherical crown shape of the silicone hydrogel used in the present invention preferably has a thickness of 0.02 mm to 1 mm at the center portion. In particular, in cases of use as a soft contact lens, the thickness is more preferably 0.05 mm to 0.5 mm. The spherical crown shape still more preferably has a thickness of 0.06 mm to 0.2 mm. The lower limit is preferably 0.04 mm, more preferably 0.05 mm, still more preferably 0.07 mm. The upper limit is preferably 0.2 mm, more preferably 0.18 mm, still more preferably 0.15 mm. Any combination of the upper limit and the lower limit may be employed.

The silicone hydrogel used in the present invention is preferably less likely to be torn in hydrous state. Since such a material, which is less likely to be torn, exhibits excellent operability during scrubbing, wearing, and removal, it is important for uses such as soft contact lenses. Unlikeliness of tearing in hydrous state can be evaluated by measuring the tensile elongation at break in hydrous state.

The silicone hydrogel used in the present invention preferably has a tensile elongation at break within the range of 200% to 1000% in hydrous state. In cases where the tensile elongation at break in hydrous state is not less than 200%, the silicone hydrogen has flexibility, does not cause discomfort during use, and can be easily handled during scrubbing, wearing, and removal, which is preferred. On the other hand, in cases where the tensile elongation at break in hydrous state is not more than 1000%, the shape recovery performance is excellent, which is preferred. The lower limit is preferably 200%, more preferably 220%, still more preferably 230%, still more preferably 250%. The upper limit is preferably 1000%, more preferably 800%, still more preferably 600%, still more preferably 500%. Any combination of the upper limit and the lower limit may be employed.

The silicone hydrogel used in the present invention preferably has flexibility so that the eyeball is not stimulated during use. The flexibility can be evaluated by measuring the tensile elastic modulus in hydrous state.

The silicone hydrogel used in the present invention preferably has a tensile elastic modulus within the range of 0.1 MPa to 1.5 MPa in hydrous state. When the tensile elastic modulus in hydrous state is not less than 0.1 MPa, the contact lens can maintain a spherical crown shape. When the tensile elastic modulus is not more than 1.5 MPa, the eyeball is less likely to be stimulated after wearing the lens, so that the comfort is less likely to be poor. The lower limit is preferably 0.1 MPa, more preferably 0.25 MPa, still more preferably 0.35 MPa, still more preferably 0.4 MPa, especially preferably 0.48 MPa. The upper limit is preferably 1.5

MPa, more preferably 1.4 MPa, still more preferably 1.2 MPa, still more preferably 1 MPa. Any combination of the upper limit and the lower limit may be employed.

The tensile elongation at break in hydrous state and the tensile elastic modulus in hydrous state can be measured by taking out a test piece of borate buffer, and, within 10 seconds thereafter, lightly wiping off the borate buffer from the surface with a clean cloth at room temperature of 20° C. and a humidity of 50%, followed, within 1 minute thereafter, by applying the test piece to a tensile tester such as Tensilon at room temperature of 20° C. and a humidity of 50%.

The silicone hydrogel used in the present invention preferably shows only a small change in the tensile elastic modulus due to hardening by drying. More specifically, the tensile elastic modulus in hydrous state is preferably within the above-described preferred range, and the change in the tensile elastic modulus due to drying is preferably small. From the viewpoint of having flexibility so that the human body is less likely to be damaged, the dry elastic modulus ratio represented by the following Equation 1 is preferably 0.1 to 10.

Dry elastic modulus ratio=the tensile elastic modulus in dry state/tensile elastic modulus in hydrous state. (1)

The lower limit is preferably 0.1, more preferably 0.5, still more preferably 1, still more preferably 1.2, especially preferably 1.5. The upper limit is preferably 10, more preferably 7, still more preferably 5, still more preferably 3, especially preferably 2.5. Any combination of the upper limit and the lower limit may be employed.

The term "(meth)" used in the present description means optional methyl substitution. Accordingly, for example, the term "(meth)acrylate" means both methacrylate and acrylate. The same applies to the terms "(meth)acrylamide", "(meth)acryloyl", and the like.

The term "(meth)acrylate" used in the present description represents (meth)acrylic acid ester.

The term "monomer" used in the present description means a compound having one or more radically polymerizable functional groups.

The term "monomer composition" used in the present description means a mixture of radically polymerizable monomers before being subjected to polymerization, a polymerization initiator, a solvent, and/or the like.

The term "repeat unit" used in the present description represents one unit of a repetitive structure derived from a monomer structure.

Here, the "repeat unit derived from a monomer" in the present invention is described. In the present invention, the "repeat unit derived from a monomer" is a structural unit in a polymer obtained when a radically polymerizable monomer is polymerized, which structural unit is produced by changing of a radically polymerizable functional group by the polymerization reaction, and corresponds to the structure of the monomer. In other words, the "repeat unit derived from a monomer" is a structural unit obtained when a radically polymerizable monomer represented by the following Formula (x) is polymerized, which structural unit is produced by changing of a radically polymerizable functional group by the polymerization reaction, and represented by the following Formula (y).

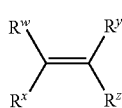
(x)

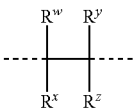
(y)

In the Formulae (x) and (y), $R^w$, $R^x$, $R^y$, and $R^z$ are not limited as long as they are independently a group with which the monomer represented by the Formula (x) can be a monomer having radical polymerizability.

The silicone hydrogel used in the present invention preferably contains a repeat unit (A) derived from a monomer represented by General Formula (I).

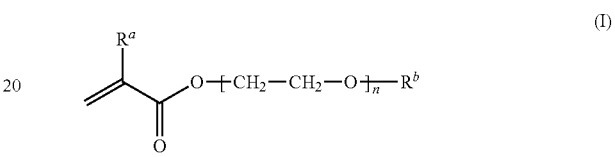
(I)

In General Formula (I), $R^a$ represents a hydrogen atom or a methyl group; and $R^b$ represents one selected from the group consisting of a hydrogen atom, a sulfonic group, a phosphate group, and an organic group having from 1 to 15 carbon atoms. "n" represents an integer within the range of 1 to 40.

The silicone hydrogel used in the present invention may contain a repeat unit (A) derived from a monomer represented by General Formula (I), which repeat unit (A) has a distribution within the range of n described above.

Although the repeat unit (A) is hydrophilic, it does not have a functional group capable of hydrogen bonding with each other. Therefore, since interactions between functional groups due to hydrogen bonds are weak, the repeat unit (A) has a property which does not easily allow hardening in dry state. It can thus be preferably used. In particular, a structure containing a (poly)ethylene glycol chain is useful since it effectively reduces the elastic modulus in dry state. Since the repeat unit (A) as a homopolymer has a glass transition temperature of not more than room temperature, the tensile elastic modulus in dry state can be lowered.

From the viewpoint of excellent polymerizability and availability, $R^a$ in General Formula (I) is preferably a hydrogen atom or a methyl group. It is more preferably a hydrogen atom because of its tendency to give a relatively low tensile elastic modulus.

As "n" in General Formula (I), an integer within the range of 1 to 40 is preferably used. In cases where n is not more than 40, the silicone hydrogel is less likely to become cloudy due to poor compatibility with other monomers, and less likely to be easily torn due to low cross-linking density of the whole silicone hydrogel. The upper limit of n is preferably 40, more preferably 25, still more preferably 12, still more preferably 10.

"n" may have a distribution. In the present invention, having a distribution means a state where a number (n in the present case) representing repeating of a certain structural unit is not limited to a single value, and where substances exhibiting a plurality of values coexist. In cases where n has a distribution, n is determined based on the number average molecular weight of the monomer represented by General Formula (I).

As $R^b$ in General Formula (I), any of a hydrogen atom, a sulfonic group, a phosphate group, and an organic group having from 1 to 15 carbon atoms may be used. From the view point of reducing interactions such as hydrogen bonding and π-π stacking, and of suppressing an increase in the tensile elastic modulus in dry state, $R^b$ is preferably an alkyl group having from 1 to 15 carbon atoms, more preferably the structure of any of an ethylhexyl group, a butyl group, a propyl group, an ethyl group, and a methyl group, still more preferably the structure of any of a propyl group, an ethyl group, and a methyl group, still more preferably an ethyl group or a methyl group.

The structure of $R^b$ may have a cyclic structure such as a furfuryl group or a crown ether.

In cases where $R^a$ is a hydrogen atom, the structure of $R^b$ may have one aromatic ring. For example, a group derived from 2-phenoxyethyl acrylate, 2-(2-phenoxyethoxy)ethyl acrylate, or the like may be used. Here, similarly to the above-described "repeat unit derived", the "group derived" means a group obtained when a radically polymerizable monomer is bound, which group is produced by changing of a radically polymerizable functional group by the polymerization reaction, and corresponds to the structure of the monomer.

The structure of $R^b$ may have a fluorine-substituted alkyl group. For example, a group derived from 2-(2,2,2-trifluoroethoxy)ethyl acrylate, heptafluorobutoxy)ethyl acrylate, or the like may be used.

For increasing wettability of the silicone hydro gel, a structure containing a sulfonic group or a phosphate group may be used as $R^b$. An organic acid structure such as a carboxyl group may also be contained.

Monomers represented by the General Formula (I) may be used individually, or a plurality of kinds monomers may be used in combination.

The silicone hydrogel used in the present invention preferably comprises the repeat unit (A) in an amount within the range of 5% by mass to 50% by mass with respect to the total mass of the silicone hydrogel in dry state. In cases where the amount of the repeat unit (A) is not less than 5% by mass, the elastic modulus in dry state is not too high. In cases where the amount is not more than 50% by mass, the oxygen permeability does not become insufficient. The lower limit is preferably 5% by mass, more preferably 7% by mass, still more preferably 10% by mass, still more preferably 12% by mass. The upper limit is preferably 50% by mass, more preferably 45% by mass, still more preferably 40% by mass, still more preferably 35% by mass. Any combination of the upper limit and the lower limit may be employed.

In the present invention, the silicone monomer means a monomer containing a polymerizable group and a siloxanyl group. The siloxanyl group means a group containing at least one Si—O—Si bond. In the silicone hydrogel used in the present invention, silicone (meth)acrylate or silicone (meth)acrylamide may be preferably used as a silicone monomer. Silicone (meth)acrylate is preferably used since it is relatively easily available.

In the present invention, the silicone (meth)acrylate means a monomer containing a (meth)acryloyloxy group and a siloxanyl group. The silicone (meth)acrylamide means a monomer containing a (meth)acrylamide group and a siloxanyl group.

In the present invention, "monofunctional" means that there is only one radically polymerizable functional group [for example, (meth)acryloyloxy group] in the molecule.

The "linear silicone" in the monofunctional linear silicone monomer in the present invention means a structure in which, when the silicon atom bound to the organic group containing a (meth)acryloyloxy group or a (meth)acrylamide group is regarded as the origin, and when a line is drawn therefrom along the siloxanyl bonds (bonds formed by —Si—O— repeats) of the silicone, the line is formed in the shape of a single line without branching. In other words, the monofunctional linear silicone monomer means a structure represented by the following General Formula (p).

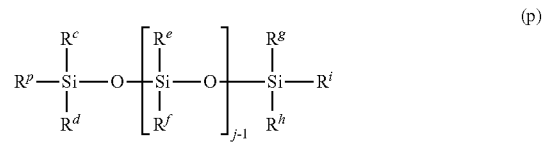

(p)

In Formula (p), $R^p$ represents an alkyl group containing a (meth)acryloyloxy group or a (meth)acrylamide group. $R^c$ to $R^i$ represent groups containing no silicon atom, and j represents an integer of 1 or more.

In the present invention, the branched silicone monomer means a structure in which, when the silicon atom bound to the organic group containing a (meth)acryloyloxy group, or a (meth)acrylamide group is regarded as the origin, and when lines are drawn therefrom along the siloxanyl bonds, the lines extend toward two or more directions, and/or have at least one branch and cannot be expressed as a single line. Known representative examples of the branched silicone monomer include 3-[tris(trimethylsiloxy)silyl]propyl methacrylate (abbreviation: TRIS). In some cases, branched silicone monomers have poor shape recovery performance, give relatively high elastic moduli compared to linear silicone monomers, and cause cloudiness due to the problem of compatibility.

The silicone hydrogel used in the present invention preferably contains a repeat unit (B) derived from a monofunctional linear silicone monomer.

The inclusion of the repeat unit (B) is preferred for giving excellent oxygen permeability. It is also important for giving excellent flexibility, and giving elastic mechanical properties which suppress tearing.

The silicone hydrogel used in the present invention preferably comprises the repeat unit (B) derived from a monofunctional linear silicone monomer in an amount within the range of 20% by mass to 70% by mass with respect to the total mass of the silicone hydrogel in dry state. In cases where the amount of the repeat unit (B) is not less than 20% by mass, sufficient oxygen permeability can be obtained. In cases where the amount is not more than 70% by mass, for example, adhesion of proteins and lipids due to decrease in wettability and increase in hydrophobicity can be suppressed. The lower limit is preferably 20% by mass, more preferably 25% by mass, still more preferably 30% by mass, still more preferably 35% by mass. The upper limit is preferably 70% by mass, more preferably 65% by mass, still more preferably 60% by mass, still more preferably 55% by mass. Any combination of the upper limit and the lower limit may be employed.

In the silicone hydrogel used in the present invention, silicone (meth)acrylate is preferably used as a monofunctional linear silicone monomer. Examples of such a monomer include those represented by the following General Formula (a).

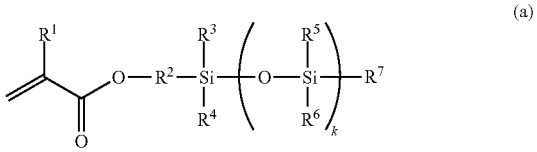
(a)

In General Formula (a), $R^1$ represents a hydrogen atom or a methyl group. $R^2$ represents a $C_1$-$C_{20}$ divalent organic group. $R^3$ to $R^6$ each independently represent a $C_1$-$C_{20}$ alkyl group or a $C_6$-$C_{20}$ aryl group. $R^7$ represents a $C_1$-$C_{20}$ alkyl group which is optionally substituted, or a $C_6$-$C_{20}$ aryl group which is optionally substituted. "k" represents an integer of 1 to 200 which optionally has a distribution.

In General Formula (a), $R^1$ represents a hydrogen atom or a methyl group. In particular, from the viewpoint of availability, a methyl group is more preferred.

In General Formula (a), $R^2$ represents a $C_1$-$C_{20}$ divalent organic group.

Examples of the organic group include alkylene groups such as methylene, ethylene, propylene, butylene, pentylene, octylene, decylene, dodecylene and octadecylene; and arylene groups such as phenylene and naphthylene. These alkylene groups and arylene groups may be either linear or branched. In cases where the number of carbon atoms in the divalent organic group is not more than 20, a decrease in compatibility with hydrophilic monomers can be suppressed. In cases where the number is not less than 1, the risk of tearing due to decreased extensibility of the silicone hydrogel obtained can be reduced. Thus, the number of carbon atoms is more preferably 1 to 12, most preferably 2 to 8. In the divalent organic group, the alkylene unit may be substituted with an oxygen atom or a sulfur atom, and each hydrogen atom adjacent to a carbon atom may be substituted with hydroxyl group, an amino group, a halogen atom, or the like. Preferred examples of the substituent in cases where the divalent organic group is substituted include substituents such as hydroxyl group, carboxyl group, sulfonic group, phosphate group, an ester, an ether, and an amide, and combinations thereof. Among these, from the viewpoint of suppressing degradation at the silicone portion, hydroxyl group, an ester, an ether, and an amide are preferred. From the viewpoint of increasing transparency of the resulting silicone hydrogel, hydroxyl group and an ether are more preferred.

More preferred examples of $R^2$ include an ethylene group, a propylene group, a butylene group, and the divalent organic groups represented by the following Formulae (a1) to (a4).

 (a1)

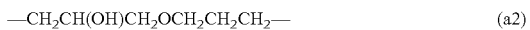 (a2)

 (a4)

 (a4)

Among these, propylene group and the divalent organic groups represented by (a1) to (a4) are preferred. Propylene group and the divalent organic group represented by (a2) are especially preferred.

In General Formula (a), $R^3$ to $R^6$ each independently represent a $C_1$-$C_{20}$ alkyl group which is optionally substituted, or a $C_6$-$C_{20}$ aryl group which is optionally substituted. Examples of these groups include methyl, ethyl, n-propyl, isopropyl, n-butyl, s-butyl, t-butyl, n-pentyl, isopentyl, s-pentyl, neopentyl, hexyl, heptyl, octyl, nonyl, decyl, dodecyl, eicosyl, phenyl, and naphthyl. These alkyl groups and aryl groups may be either linear or branched. In cases where each group is a $C_1$-$C_{20}$ alkyl group which is optionally substituted, or a $C_6$-$C_{20}$ aryl group which is optionally substituted, a decrease in oxygen permeability of the resulting silicone hydrogel due to a decreased relative silicone content and the like can be suppressed. Thus, the number of carbon atoms is more preferably 1 to 12, still more preferably 1 to 6, still more preferably 1 to 4. In cases where the alkyl group or the aryl group is substituted, examples of the substituent include aldehyde, carboxyl, alcohol, alkoxy, ether, halogen, alkylene glycol, alkyl thioether, amino, nitro, cyano, sulfate, and phosphate.

In General Formula (a), $R^7$ represents a $C_1$-$C_{20}$ alkyl group which is optionally substituted, or a $C_6$-$C_{20}$ aryl group which is optionally substituted. In cases where the number of carbon atoms of $R^7$ is not less than 1, hydrolysis of the polysiloxane chain can be suppressed, while in cases where the number of carbon atoms is not more than 20, a decrease in oxygen permeability of the silicone hydrogel can be prevented. Thus, $R^7$ is more preferably an alkyl group having 1 to 10 carbon atoms or an aryl group having 6 to 10 carbon atoms, still more preferably an alkyl group having 1 to 6 carbon atoms, still more preferably an alkyl group having 1 to 4 carbon atoms. Preferred examples of the $C_1$-$C_{20}$ alkyl group and the $C_6$-$C_{20}$ aryl group include methyl, ethyl, n-propyl, isopropyl, n-butyl, s-butyl, t-butyl, n-pentyl, isopentyl, s-pentyl, neopentyl, hexyl, heptyl, octyl, nonyl, decyl, dodecyl, eicosyl, phenyl, and naphthyl. These alkyl groups and aryl groups may be either linear or branched. In cases where the alkyl group or the aryl group is substituted, examples of the substituent include aldehyde, carboxyl, alcohol, alkoxy, ether, halogen, alkylene glycol, alkyl thioether, amino, nitro, cyano, sulfate, and phosphate.

In General Formula (a), "k" represents an integer of 1 to 200 which optionally has a distribution. In cases where k is not more than 200, for example, a decrease in compatibility with hydrophilic monomers due to an excessive proportion of the hydrophobic silicone portion can be easily suppressed. In cases where k is not less than 1, oxygen permeability and shape recovery performance can be obtained. Thus, k is more preferably 1 to 100, still more preferably 2 to 50, especially preferably 3 to 20. The lower limit is preferably 1, more preferably 2, still more preferably 3. The upper limit is preferably 200, more preferably 100, still more preferably 50, still more preferably 20. Any combination of the lower limit and the upper limit may be employed. In cases where k has a distribution, k is determined based on the number average molecular weight of the monofunctional linear silicone monomer. In the silicone hydrogel used in the present invention, a single kind of monofunctional linear silicone monomer may be used, or a plurality of kinds of monofunctional linear silicone monomers having different "k"s may be used in combination. The monofunctional linear silicone monomer used in the silicone hydrogel used in the present invention may be a combination of a plurality of kinds of monofunctional linear silicone monomers that are different from each other in chemical structures other than k.

The silicone hydrogel used in the present invention preferably contains a repeat unit (C) derived from a monomer containing an amide structure. The repeat unit (C) is used for giving the silicone hydrogel an appropriate water content. Since, in some cases, contribution of the repeat unit (A) to the water content is not very large, the repeat unit (C) is preferably used as an aid therefor.

In the present invention, the amide structure means the structure represented by the following Formula (q). For example, amide compounds, imide compounds, and urea compounds, and derivatives thereof contain the amide structure.

(q)

The amide structure is less likely to be hydrolyzed compared to an ester bond or the like. It can therefore produce excellent durability, and, even in severe environments such as steam sterilization, the amide structure can be expected to suppress degradation, elimination, deterioration, and the like of part of the polymer structure. Further, the amide structure is preferred since it gives excellent hydrophilicity and lubrication.

The repeat unit (C) is preferably derived from a monomer represented by the following General Formula (II-1) or General Formula (II-2).

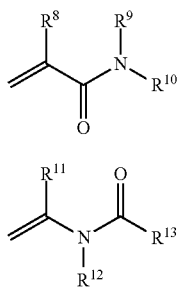

In General Formula (II-1) and General Formula (II-2), $R^8$ and $R^{11}$ each independently represent a hydrogen atom or a methyl group; $R^9$ and $R^{10}$, and $R^{12}$ and $R^{13}$ represent a hydrogen atom(s), and/or a $C_2$-$C_{20}$ alkyl group(s) which is/are either branched or linear, which optionally contain(s) a cyclic structure, and which is/are optionally substituted; and $R^{12}$ and $R^{13}$ optionally bind to each other to form a ring. In cases where the alkyl group is substituted, examples of the substituent include aldehyde, carboxyl, alcohol, alkoxy, ether, halogen, alkylene glycol, alkyl thioether, amino, nitro, cyano, sulfate, and phosphate.

Here, in view of suppressing loss of hydrophilicity which contributes to an increase in the water content, $R^9$ and $R^{19}$ are preferably each independently a hydrogen atom or a branched or linear alkyl group. In cases of an alkyl group, the alkyl group has preferably 1 to 6 carbon atoms, more preferably 1 to 4 carbon atoms, still more preferably 1 to 2 carbon atoms.

Similarly, in view of suppressing loss of hydrophilicity which contributes to an increase in the water content, $R^{12}$ and $R^{13}$ are preferably each independently a hydrogen atom or a branched or linear alkyl group. $R^{12}$ and $R^{13}$ more preferably bind to each other to form a ring. In cases of an alkyl group, the alkyl group has preferably 1 to 6 carbon atoms, more preferably 1 to 4 carbon atoms, still more preferably 1 to 2 carbon atoms. In cases where $R^{12}$ and $R^{13}$ bind to each other to form a ring, from the viewpoint of suppressing loss of structural stability, the sum of the numbers of carbon atoms of $R^{12}$ and $R^{13}$ is preferably 3 to 6, more preferably 3 to 5, still more preferably 3 to 4.

The silicone hydrogel used in the present invention preferably comprises the repeat unit (C) in an amount within the range of 5% by mass to 50% by mass with respect to the total mass of the silicone hydrogel in dry state. In cases where the amount of the repeat unit (C) is not less than 5% by mass, a sufficient water content can be obtained, and the wettability is not poor. In cases where the amount is not more than 50% by mass, a decrease in the oxygen permeability, imbalance of the compatibility leading to occurrence of cloudiness, deterioration of strength of the gel due to excessive swelling, and the like can be reduced. The lower limit is preferably 5% by mass, more preferably 8% by mass, still more preferably 10% by mass, still more preferably 12% by mass. The upper limit is preferably 50% by mass, more preferably 45% by mass, still more preferably 40% by mass, still more preferably 35% by mass. Any combination of the upper limit and the lower limit may be employed.

Examples the repeat unit (C) which can be preferably used include, as the monomer from which the repeat unit (C) is derived, compounds containing at least one of vinyl amide, vinyl imide, vinyl lactam, hydrophilic (meth)acrylate, (meth)acrylamide and derivatives thereof (examples of the derivatives include N,N-dimethylacrylamide, N,N-diethylacrylamide, and N-hydroxyethylacrylamide), hydrophilic styrene compounds, vinyl ether, vinyl carbonate, vinyl carbamate, and vinyl urea.

Specific examples of these preferred monomers include (meth)acrylamides, N-vinyl carboxylic acid amides, cyclic N-vinyl lactams, cyclic N-vinyl pyridines, and N-vinyl imidazoles. (Meth)acrylamides are especially preferred because of their excellent hydrophilicity.

Preferred specific examples of the monomer from which the repeat unit (C) can be obtained include acrylamide, N-methylacrylamide, N-ethylacrylamide, N-isopropylacrylamide, N,N-dimethylacrylamide, N,N-diethylacrylamide, N,N-diisopropylacrylamide, acryloylmorpholine, diacetone acrylamide, N-vinylformamide, N-vinylacetamide, N-vinyl-N-methylacetamide, N-vinylpyrrolidone, N-vinyl-2-piperidone, N-vinyl-2-caprolactam, N-vinyl-3-methyl-2-caprolactam, N-vinyl-4-methyl-2-caprolactam, 2-ethyloxazoline, N-(2-hydroxypropyl)(meth)acrylamide, N-(2-hydroxyethyl)(meth)acrylamide, 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), 3-((3-methacryloyloxy)propyl)dimethylammonio)propane-1-sulfonate (MAPDAPS), N-vinyl-2-methylpropionamide, N-vinyl-N,N'-dimethylurea, dimethylaminopropyl (meth)acrylamide, dimethylaminoethyl (meth)acrylamide, dimethylaminopropyl (meth)acrylate, and dimethylaminoethyl (meth)acrylate.

Among these, from the viewpoint of obtaining a hydrophilic polymer having excellent wettability and lubrication, N-methylacrylamide, N,N-dimethylacrylamide, N-vinylpyrrolidone, N-vinylcaprolactam, N-vinylacetamide, and N-vinyl-N-methylacetamide are more preferred. These may be used individually, or two or more of these may be used in combination.

The monomers represented by the General Formula (II-1) or General Formula (II-2) may be used individually, or a plurality of kinds of monomers may be used in combination.

The silicone hydrogel used in the present invention is preferably a polymer comprising the repeat unit (A) derived from a monomer represented by the General Formula (I), the repeat unit (B) derived from a monomer represented by the General Formula (a), and the repeat unit (C) derived from a monomer represented by the General Formula (II-1) or General Formula (II-2). Here, the symbols in the General Formulae are defined as described above, and preferred examples of those symbols are also as described above. Further, as described above, each of the repeat units may be either a single kind of unit or a combination of a plurality of kinds of units.

Preferably, in the polymer comprising the repeat units (A), (B), and (C), the repeat unit (A) is contained in an amount within the range of 5% by mass to 50% by mass with respect to the total mass of the silicone hydrogel in dry state; the repeat unit (B) is contained in an amount within the range of 20% by mass to 70% by mass with respect to the total mass of the silicone hydrogel in dry state; and the repeat unit (C) is contained in an amount within the range of 5% by mass to 50% by mass with respect to the total mass of the silicone hydrogel in dry state. However, of course, the total of the repeat units (A), (B), and (C) does not exceed 100% by mass with respect to the total mass of the silicone hydrogel in dry state. In this polymer, the total of the repeat units (A), (B), and (C) is preferably more than 50% by mass, more preferably not less than 70% by mass, still more preferably not less than 85% by mass, with respect to the total mass of the silicone hydrogel in dry state.

The silicone hydrogel used in the present invention may contain a repeat unit derived from a polyfunctional monomer having two or more polymerizable groups (cross-linking monomer). In this case, the silicone hydrogel used in the present invention has a solvent resistance. Preferred examples of the polyfunctional monomer having two or more polymerizable groups include ethylene glycol di(meth)acrylate; diethylene glycol di(meth)acrylate; triethylene glycol di(meth)acrylate; tetraethylene glycol di(meth)acrylate; neopentyl glycol di(meth)acrylate; tetraethylene glycol di(meth)acrylate; 1,3-bis(3-(meth)acryloyloxypropyl)-1,1,3,3-tetramethyl-disiloxane; 1,3-bis(3-(meth)acryloyloxypropyl)-1,1,3,3-tetrakis(trimethylsiloxy)disiloxane; polydimethylsiloxanes having (meth)acryloyloxy groups at both ends, such as X-22-164A, manufactured by Shin-Etsu Chemical Co., Ltd., and "Silaplane" (registered trademark) FM7711, manufactured by JNC Corporation; bifunctional or polyfunctional (meth)acrylates such as glyceryl tri(meth)acrylate, pentaerythritol tetra(meth)acrylate, and trimethylolpropane tri(meth)acrylate; and bisacrylamides such as N,N'-methylene bisacrylamide, N,N'-ethylene bisacrylamide, and N,N'-propylene bisacrylamide.

Among these, from the viewpoint of easily obtaining a silicone hydrogel having a low tensile elastic modulus, bifunctional (meth)acrylates are preferred. From the viewpoint of increasing the shape recovery performance of the resulting silicone hydrogel, silicone-based di(meth)acrylates, such as 1,3-bis(3-(meth)acryloyloxypropyl)-1,1,3,3-tetramethyl-disiloxane; 1,3-bis(3-(meth)acryloyloxypropyl)-1,1,3,3-tetrakis(trimethylsiloxy)disiloxane; and polydimethylsiloxanes having (meth)acryloyloxy groups at both ends, including X-22-164A, X-22-164B, and X-22-164C, manufactured by Shin-Etsu Chemical Co., Ltd., and "Silaplane" (registered trademark) FM7711 and FM7721, manufactured by JNC Corporation; are more preferred.

In cases where the amount of repeat units derived from the polyfunctional monomer having two or more polymerizable groups is not more than 25% by mass, the silicone hydrogel is less likely to be too hard. In cases where the amount is not less than 0.1% by mass, difficulty in maintenance of the shape of the silicone hydrogel can be avoided. Thus, the amount is preferably 0.1 to 25% by mass, more preferably 0.5 to 20% by mass, most preferably 0.8 to 12% by mass, with respect to the mass of the silicone hydrogel. The lower limit is preferably 0.1% by mass, more preferably 0.5% by mass, still more preferably 1% by mass, still more preferably 5% by mass. The upper limit is preferably 25% by mass, more preferably 20% by mass, still more preferably 15% by mass, still more preferably 12% by mass. Any combination of the lower limit and the upper limit may be employed.

In the silicone hydrogel used in the present invention, at least one of the repeat unit (A) derived from a monomer represented by General Formula (I) and the repeat unit (C) derived from a monomer containing an amide structure preferably has a glass transition temperature of not more than 20° C. in a state of a homopolymer.

In cases where the glass transition temperature is not more than room temperature in the state of homopolymer, the tensile elastic modulus in dry state can be lowered, which is preferred. The repeat unit (A) can be preferably used since it has a glass transition temperature of not more than room temperature in homopolymer state in most cases. Similarly, the repeat unit (C) more preferably has a glass transition temperature of not more than room temperature in homopolymer state. At least one of the repeat unit (A) and the repeat unit (C) preferably has such a property.

The glass transition temperature in homopolymer state can be measured by synthesizing the homopolymer by an arbitrary method using the monomer to be analyzed, and then performing the measurement using a differential scanning calorimeter (DSC).

The silicone hydrogel used in the present invention may be molded alone into a desired shape, or may be molded after blending with other materials. A coating may be applied to the surface of the molded article.

In cases where the silicone hydrogel used in the present invention is molded to be used as an ophthalmic lens, the polymerization method and the molding method may be standard methods as follows. Examples of the methods include a method in which the silicone hydrogel is molded into the shape of a round bar or a plate, and then finished into a desired shape by cutting or turning; a mold polymerization method; and a spin casting method.

A description is given below to illustrate an example of the case where an ophthalmic lens is prepared by mold polymerization from the silicone hydrogel used in the present invention.

A monomer composition is injected into a gap between two molds having a lens shape. Subsequently, photopolymerization or thermal polymerization is carried out to perform molding into a lens shape. The molds are those prepared with a resin, glass, ceramic, metal, or the like. In cases of photopolymerization, a material that passes a photopolymerization wavelength is used. Usually, a resin or a glass is used. When a silicone hydrogel is produced, a monomer composition is injected into a gap formed with two opposing molds. Subsequently, the molds whose gap is filled with the monomer composition are irradiated with an active ray such as an ultraviolet ray or a visible ray, or a combination thereof, or are heated in an oven or a liquid bath, to allow polymerization of the monomers. The method may also be carried out by combination of photopolymerization and thermal polymerization, for example, by performing photopolymerization first, and then performing thermal polymerization, or, conversely, by performing thermal polymerization first, and then performing photopolymerization.

In general, in cases of the photopolymerization, a light including a high-level light from a light source such as a mercury lamp or a fluorescent lamp is radiated for a short period (usually for not more than 1 hour). In cases where thermal polymerization is carried out, the temperature is preferably slowly increased from about room temperature to a high temperature of 60° C. to 200° C. for several hours to several tens hours from the viewpoint of maintaining optical homogeneity and quality of the polymer, and increasing the reproducibility.

Various organic and inorganic solvents are applicable as the polymerization solvent. Examples of the polymerization solvent include water; alcoholic solvents such as methanol, ethanol, propanol, 2-propanol, butanol, tert-butanol, tert-amyl alcohol, 3,7-dimethyl-3-octanol, and tetrahydrolinalool; aromatic hydrocarbon solvents such as benzene, toluene, and xylene; aliphatic hydrocarbon solvents such as hexane, heptane, octane, decane, petroleum ether, kerosene, ligroin, and paraffin; ketone solvents such as acetone, methyl ethyl ketone, and methyl isobutyl ketone; ester solvents such as ethyl acetate, butyl acetate, methyl benzoate, dioctyl phthalate, and ethylene glycol diacetate; and glycol ether solvents such as diethyl ether, tetrahydrofuran, dioxane, ethylene glycol dialkyl ether, diethylene glycol dialkyl ether, triethylene glycol dialkyl ether, tetraethylene glycol dialkyl ether, polyethylene glycol dialkyl ether, polyethylene glycol-polypropylene glycol block copolymers, and polyethylene glycol-polypropylene glycol random copolymers. These may be used either individually or as a mixture. Among these, from the viewpoint of suppressing inhibition of radical polymerization, water, tent-butanol, tent-amyl alcohol, and 3,7-dimethyl-3-octanol are preferred. Water is most preferred.

When the silicone hydrogel used in the present invention is obtained by polymerization, a polymerization initiator may be added for promotion of the polymerization. Preferred examples of the initiator include thermal polymerization initiators such as peroxides and azo compounds; photopolymerization initiators (including those for UV light or visible light, or a combination thereof); and mixtures thereof. When thermal polymerization is carried out, a thermal polymerization initiator having an optimal degradation property for a desired reaction temperature is selected and used. In general, azo initiators and peroxide initiators having a 10-hour half-life temperature of 40° C. to 120° C. are preferred. Examples of the photopolymerization initiator include carbonyl compounds, peroxides, azo compounds, sulfur compounds, halogen compounds, and metal salts.

Specific examples of the photoinitiator include aromatic a-hydroxy ketones, alkoxyoxybenzoins, acetophenone, acylphosphine oxide, bisacylphosphine oxide, and tertiary amine+diketone, and mixtures thereof. More specific examples of the photoinitiator include 1-hydroxy cyclohexyl phenyl ketone, 2-hydroxy-2-methyl-1-phenyl-propan-1-one, bis(2,6-dimethoxybenzoyl)-2,4-4-trimethylpentylphosphine oxide (DMBAPO), bis(2,4,6-trimethylbenzoyl)-phenylphosphine oxide ("Irgacure" (registered trademark) 819), 2,4,6-trimethylbenzyldiphenyl phosphine oxide, and 2,4,6-trimethylbenzoyldiphenyl phosphine oxide, benzoin methyl ether, and combination of camphorquinone and ethyl 4-(N,N-dimethylamino)benzoate.

Examples of commercially available visible light photoinitiator systems include "Irgacure" (registered trademark) 819, "Irgacure" (registered trademark) 1700, "Irgacure" (registered trademark) 1800, "Irgacure" (registered trademark) 1850 (these are manufactured by BASF), and Lucirin TPO initiator (manufactured by BASF). Examples of commercially available UV photoinitiators include "Darocur" (registered trademark) 1173 and "Darocur" (registered trademark) 2959 (manufactured by BASF). These polymerization initiators may be used either individually or as a mixture, and are used in an amount within the range of 0.1% by mass to 1% by mass with respect to the total mass of the whole monomer component.

Examples of other components that may be present in the reaction mixture used for the formation of the contact lens in the present invention include ultraviolet-absorbing compounds, pharmaceutical compounds, dietary supplement compounds, antimicrobial compounds, and copolymerized or non-polymeric dyes, including dyes and compounds whose color reversibly changes or which reflect light when they are exposed to lights with various wavelengths, mold release agents, reactive dyes, pigments, or combinations thereof.

The silicone hydrogel used in the present invention can be modified by a variety of methods. Specific examples of the modification methods include electromagnetic wave (including light) irradiation; plasma irradiation; vapor deposition; chemical vapor deposition treatments such as sputtering; heating; mold-transfer coating; base treatment; acid treatment; and treatment with other suitable surface treatment agents. These may also be used in combination.

Examples of the base treatment and the acid treatment include a method in which the molded article is brought into contact with a basic or acidic solution, and a method in which the molded article is brought into contact with a basic or acidic gas. More specific examples of the methods include a method in which the molded article is immersed in a basic or acidic solution, a method in which a basic or acidic solution, or a basic or acidic gas, is sprayed on the molded article, a method in which a basic or acidic solution is applied to the molded article with a spatula, brush, or the like, a method in which the molded article is spin-coated with a basic or acidic solution, and a dip coating method. A method with which a high modification effect can be most simply obtained is a method in which the molded article is immersed in a basic or acidic solution.

The temperature during the immersion of the silicone hydrogel in the basic or acidic solution is not limited. The temperature is usually within the range of −50° C. to 300° C. From the viewpoint of workability, the temperature is preferably within the range of −10° C. to 150° C., more preferably within the range of −5° C. to 60° C., still more preferably within the range of 0° C. to 40° C.

Although the optimal length of time of the immersion of the silicone hydrogel in the basic or acidic solution varies depending on the temperature, it is generally preferably not more than 100 hours, more preferably not more than 24 hours, most preferably not more than 12 hours, from the viewpoint of preventing deterioration of workability and productivity, and preventing production of adverse effects such as a decrease in the oxygen permeability or deterioration of mechanical properties, caused by a prolonged contacting time.

Examples of the bases that may be used include alkali metal hydroxides, alkaline earth metal hydroxides, various carbonates, various borates, various phosphates, ammonia, various ammonium salts, various amines, and high-molecular-weight bases such as polyethylenimine and polyvinylamine. Among these, alkali metal hydroxides are most preferred since they are inexpensive and produce high treatment effects.

Examples of the acids that may be used include various inorganic acids such as sulfuric acid, phosphoric acid, hydrochloric acid, and nitric acid; various organic acids such as acetic acid, formic acid, benzoic acid, and phenol; and high-molecular-weight acids such as polyacrylic acid and polystyrene sulfonic acid. Among these, high-molecular-weight acids are most preferred since they produce high treatment effects, and their adverse effects on other physical properties are minimal.

The solvent of the basic or acidic solution may be either an inorganic or organic solvent. Examples of the solvent include water; methanol, ethanol, propanol, 2-propanol, butanol, ethylene glycol, diethylene glycol, triethylene glycol, tetraethylene glycol, polyethylene glycol, glycerin, and other alcohols; benzene, toluene, xylene, and other aromatic hydrocarbons; hexane, heptane, octane, decane, petroleum ether, kerosene, ligroin, paraffin, and other aliphatic hydrocarbons; acetone, methyl ethyl ketone, methyl isobutyl ketone, and other ketones; ethyl acetate, butyl acetate, methyl benzoate, dioctyl phthalate, and other esters; diethyl ether, tetrahydrofuran, dioxane, ethylene glycol dialkyl ether, diethyl glycol dialkyl ether, triethylene glycol dialkyl ether, tetraethylene glycol dialkyl ether, polyethylene glycol dialkyl ether, and other ethers; dimethylformamide, dimethylacetamide, N-methyl-2-pyrrolidone, dimethylimidazolidinone, hexamethylphosphoric triamide, dimethyl sulfoxide, and other aprotic polar solvents; methylene chloride, chloroform, dichloroethane, trichloroethane, trichloroethylene, and other halogen-containing solvents; and chlorofluorocarbon-containing solvents. Among these, water is most preferred from the viewpoints of economic efficiency, ease of handling, chemical stability, and the like. The solvent may also be a mixture of two or more solvents.

In the present invention, the basic or acidic solution used may contain a component other than the basic or acidic substance and the solvent.

After the base treatment or acid treatment, the basic or acidic substance may be removed from the silicone hydrogel by washing. The washing solvent may be either an inorganic or organic solvent. Examples of the solvent include water; methanol, ethanol, propanol, 2-propanol, butanol, ethylene glycol, diethylene glycol, triethylene glycol, tetraethylene glycol, polyethylene glycol, glycerin, and other alcohols; benzene, toluene, xylene, and other aromatic hydrocarbons; hexane, heptane, octane, decane, petroleum ether, kerosene, ligroin, paraffin, and other aliphatic hydrocarbons; acetone, methyl ethyl ketone, methyl isobutyl ketone, and other ketones; ethyl acetate, butyl acetate, methyl benzoate, dioctyl phthalate, and other esters; diethyl ether, tetrahydrofuran, dioxane, ethylene glycol dialkyl ether, diethylene glycol dialkyl ether, triethylene glycol dialkyl ether, tetraethylene glycol dialkyl ether, polyethylene glycol dialkyl ether, and other ethers; dimethylformamide, dimethylacetamide, N-methyl-2-pyrrolidone, dimethylimidazolidinone, hexamethylphosphoric triamide, dimethyl sulfoxide, and other aprotic polar solvents; methylene chloride, chloroform, dichloroethane, trichloroethane, trichloroethylene, and other halogen-containing solvents; and chlorofluorocarbon-containing solvents.

The washing solvent may also be a mixture of two or more solvents. The washing solvent may also contain a component other than a solvent, such as an inorganic salt, surfactant, or washing agent.

The above modification treatment may be carried out for the whole silicone hydrogel, or may be carried out only for part of the silicone hydrogel, for example, only for the surface. In cases where the modification treatment is carried out only for the surface, wettability of the surface alone can be increased without largely changing the physical properties of the whole silicone hydrogel.

The silicone hydrogel used in the present invention has a transparency of preferably 5 or 4, more preferably 5, according to visual observation. The judgment method therefor is described in the Examples below. For easier visual observation of the contact site between the medical device and the human body, a material having transparency such as the material in the present invention is suitable for use as a wound dressing. Further, infusion tubes, gas transfer tubes, stents, sheaths, cuffs, tube connectors, access ports, drainage bags, blood circuits, and the like also preferably have transparency from the viewpoint of increasing visibility of channels. In particular, ophthalmic lenses preferably have transparency so that no cloudiness occurs in the vision.

The silicone hydrogel used in the present invention has a degree of lubrication of preferably 5 or 4, more preferably 5, according to sensory evaluation by touching with a finger. The judgment method therefor is described in the following Examples.

In cases of use as an ophthalmic lens, the silicone hydrogel used in the present invention has a dynamic contact angle of preferably not more than 70°, more preferably not more than 60°, still more preferably not more than 50°, in terms of the advancing contact angle. Although the lower limit of the advancing contact angle is not limited, the lower limit is realistically about 20°.

In the present invention, the borate buffer means the "salt solution" described in Example 1 of JP 2004-517163 A. More specifically, the borate buffer is an aqueous solution prepared by dissolving 8.48 g of sodium chloride, 9.26 g of boric acid, 1.0 g of sodium borate (sodium tetraborate decahydrate), and 0.10 g of ethylenediaminetetraacetic acid in pure water such that the final volume becomes 1000 mL.

EXAMPLES

The present invention will now be concretely described by way of Examples. Before description of each example, measurement methods and evaluation methods for various properties are described.

(1) Diameter

A contact lens sample was immersed in a predetermined volume of borate buffer in a petri dish, and a magnified projection image (at a magnification of ×10) was obtained using an all-purpose projector V-10A manufactured by Nikon Corporation, followed by measuring the diameter using a ruler. The measured value was divided by 10, and the resulting value was recorded as the lens diameter.

(2) Transparency

A sample in a wet state with borate buffer was subjected to visual observation of transparency, and rated on a 5-point scale according to the following standard. 5: Not cloudy; transparent. 4: Slightly cloudy. 3: Rather cloudy; semi-transparent. 2: Cloudy; not transparent at all. 1: Completely white.

(3) Wettability

A contact lens sample was immersed in borate buffer in a beaker at room temperature (25° C.) for not less than 24 hours. The beaker containing the test piece and borate buffer was subjected to treatment with an ultrasonic washer (for 1 minute). The test piece was taken out of the borate buffer and held in air such that the diameter direction was vertically oriented. The surface condition was visually observed to measure the surface liquid film retention time.

(4) Water Content

For a contact lens sample, the mass in hydrous state (W1) and the mass in dry state (W2) were measured, and the water content was calculated according to the following equation.

Water content (%)=$(W1-W2)/W1 \times 100$ (5) Tensile Elongation at Break and Tensile Elastic Modulus in Hydrous State From a contact lens sample in hydrous state, a dumbbell-shaped sample having a width of 5 mm in the narrowest portion was cut out, and the sample prepared was subjected to measurement of the thickness using an ABC Digimatic Indicator (ID-C112, manufactured by Mitutoyo Corporation), and then to measurement of the tensile elastic modulus and the elongation at break using Tensilon (RTM-100, manufactured by Toyo Baldwin Co., Ltd.; crosshead speed, 100 mm/minute).

(6) Zero-Stress Period

From near the center of a contact lens sample in hydrous state, a strip-shaped sample having a width of 5 mm and a length of 1.5 cm was cut out, and the sample prepared was subjected to measurement using a rheometer CR-500DX manufactured by Sun Scientific Co., Ltd. An operation in which

- a sample having a width of 5 mm and a thickness within the range of 0.05 mm to 0.2 mm held at an inter-supporting-point distance of 5 mm (State A) was drawn using a load cell with a maximum load of 2 kg at a rate of 100 mm/minute until the inter-supporting-point distance became 10 mm, and then
- the inter-supporting-point distance was reduced to 5 mm at the same rate, was repeated three times while obtaining measured values at 20-millisecond intervals, and the length of time
- from the time point when the stress became zero during the second reduction of the inter-supporting-point distance to 5 mm
- to the time point when the stress became non-zero after starting the third drawing was measured.

In State A, the test piece was held such that loosening of the test piece was prevented as much as possible, and such that the stress became zero.

The range within which the stress was regarded as zero was set to a range of the measured value of −0.05 gf to 0.05 gf.

(7) Lubrication

A contact lens sample was immersed in phosphate buffer in a vial at room temperature, and subjected to steam sterilization. The sample was then taken out of the phosphate buffer, and rubbed with a human finger five times to perform sensory evaluation on the following 5-point rating scale.

5: Excellent lubrication
4: Lubrication at a level almost intermediate between 5 and 3
3: Moderate level of lubrication
2: Slight lubrication (at a level almost intermediate between 3 and 1)
1: No lubrication (8) Dynamic Contact Angle After steam sterilization, a contact lens in hydrous state was taken out of a package solution, and a strip-shaped sample having a width of 5 mm was cut out. After measuring the thickness of the outer edge portion of the lens, the lens was immersed in borate buffer, followed by performing ultrasonic washing for 20 seconds. The sample prepared was subjected to measurement of the dynamic contact angle against borate buffer using a dynamic contact angle meter WET-6000 manufactured by Rhesca Co., Ltd., wherein an operation of advancing (movement of immersing the sample in borate buffer) and receding (movement of completely taking out the sample immersed in the borate buffer) was repeated twice, and wherein the second dynamic contact angle was subjected to comparison (immersion speed, 7 mm/minute).

(9) Tensile Elastic Modulus in Dry State

From a contact lens sample in hydrous state, a dumbbell-shaped sample having a width of 5 mm in the narrowest portion was cut out, and the sample was dried in a vacuum dryer at 40° C. for not less than 16 hours to provide a sample in dry state, followed by measuring the width of the narrowest portion using a vernier caliper. Further, the thickness was measured using an ABC Digimatic Indicator (ID-C112, manufactured by Mitutoyo Corporation), and then the tensile elastic modulus was measured using Tensilon (RTM-100, manufactured by Toyo Baldwin Co., Ltd.; crosshead speed, 100 mm/minute).

(10) Oxygen Permeability

Three sheet-shaped silicone hydrogels with different thicknesses (0.26 mm, 0.52 mm, or 0.77 mm in thickness) having the composition of Example 2 were prepared by performing polymerization between glass plates. The sheet-shaped samples were processed to have a diameter of about 15 mm, and immersed in physiological saline for not less than 1 hour. Using a film oxygen permeability meter K-316 (manufactured by Tsukuba Rika Seiki Co., Ltd.), each processed sample was mounted on a jig, and placed in physiological saline bubbled with nitrogen gas. With application of a constant voltage, equilibration was allowed until the current value became stable. After the current value became stable, the bubbling gas was changed from nitrogen gas to oxygen gas. In this process, the electric current generated by electrode reaction of oxygen that permeated through the sample was recorded. The measurement was carried out at a temperature within the range of 35.0° C.±0.5° C. From the resulting value, the oxygen permeability coefficient was calculated with reference to an ISO standard (ISO18369-4:2006) and a document (Efron N et al., Optom. Vis. Sci. 2007; 84(4) 328-337), to provide an index of oxygen permeability.

(11) Lipid Adhesion Resistance

A stirring bar (36 mm) was placed in a 500-mL beaker, and 1.5 g of methyl palmitate and 500 g of pure water were placed in the beaker. The temperature of a water bath was set to 37° C., and the above beaker was placed at the center of the water bath, followed by stirring with a magnetic stirrer for 1 hour. The rotation speed was set to 600 rpm. Each sample, with a spherical crown shape (diameter of the edge portion, about 14 mm; thickness, about 0.1 mm), was placed in a basket, and then fed into the above beaker, followed by stirring in this state. One hour later, the stirring was stopped, and the sample in the basket was washed by scrubbing using tap water at 40° C. and a household liquid detergent ("Mama Lemon" (registered trademark), manufactured by Lion Corporation). The washed sample was placed in a 12-well plastic dish containing distilled water, and left to stand in a refrigerator overnight. Cloudiness of the sample was visually observed, and the amount of methyl palmitate adhering to the sample was judged according to the following standard.

5: Not cloudy; transparent
4: Slight presence of cloudy portions
3: Considerable presence of cloudy portions
2: Mostly cloudy
1: Entirely cloudy Abbreviations of the monomers and the like used in the Examples are as follows.

MEA: 2-Methoxyethyl acrylate bm200: "Blenmer" (registered trademark) PME-200, manufactured by NOF Corporation (methoxypolyethylene glycol monomethacrylate; repeat number of polyethylene glycol portion, about 4)

bm400: "Blenmer" (registered trademark) PME-400, manufactured by NOF Corporation (methoxypolyethylene glycol monomethacrylate; repeat number of polyethylene glycol portion, about 9)

TRIS: 3-[Tris(trimethylsiloxy)silyl]propyl methacrylate, manufactured by Tokyo Chemical Industry Co., Ltd.

mPDMS: Monofunctional linear silicone monomer represented by the following Formula (s1) (average molecular weight, 1000; MCR-M11, manufactured by Gelest, Inc.)

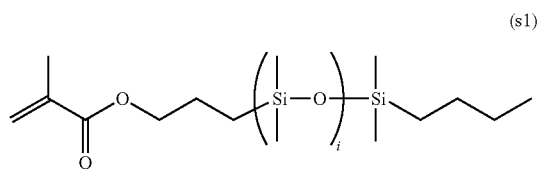

(s1)

DMAA: N,N-Dimethylacrylamide, manufactured by Tokyo Chemical Industry Co., Ltd. 164AS: Bifunctional silicone monomer X-22-164AS, manufactured by Shin-Etsu Chemical Co., Ltd. ($\alpha,\omega$-di-(3-methacryloxy-propyl)-polydimethylsiloxane); functional group equivalent, 450

164A: Bifunctional silicone monomer X-22-164A, manufactured by Shin-Etsu Chemical Co., Ltd. ($\alpha,\omega$-di-(3-methacryloxy-propyl)-polydimethylsiloxane); functional group equivalent, 860

164B: Bifunctional silicone monomer X-22-164B, manufactured by Shin-Etsu Chemical Co., Ltd. ($\alpha,\omega$-di-(3-methacryloxy-propyl)-polydimethylsiloxane); functional group equivalent, 1600

164C: Bifunctional silicone monomer X-22-164C, manufactured by Shin-Etsu Chemical Co., Ltd. ($\alpha,\omega$-di-(3-methacryloxy-propyl)-polydimethylsiloxane); functional group equivalent, 2400

3G: Triethylene glycol dimethacrylate, manufactured by Shin-Nakamura Chemical Co., Ltd.

NVP: N-Vinylpyrrolidone, manufactured by Tokyo Chemical Industry Co., Ltd.

FM0711: Monofunctional linear silicone monomer "Silaplane" (registered trademark), manufactured by JNC Corporation (polydimethylsiloxane monomethacrylate); average molecular weight, 1000

FM7721: Bifunctional silicone monomer "Silaplane" (registered trademark), manufactured by JNC Corporation ($\alpha,\omega$-di-(3-methacryloxy-propyl)-polydimethylsiloxane); average molecular weight, 5000

NB: Ultraviolet absorber 2-(2'-hydroxy-5'-methacryloyloxyethylphenyl)-2H-benzotriazole, manufactured by Tokyo Chemical Industry Co., Ltd.

RB: Coloring agent Reactive Blue 246, manufactured by Arran Chemical Co., Ltd. (1,4-bis[4-(2-methacryloxyethyl)phenylamino]anthraquinone)

IC: Photoinitiator "Irgacure" (registered trademark) 819, manufactured by Ciba Specialty Chemicals (phenylbis (2,4,6-trimethylbenzoyl)-phosphine oxide).

TAA: tent-Amyl alcohol, manufactured by Tokyo Chemical Industry Co., Ltd.

RO water: Pure water obtained by filtration through a reverse osmosis membrane

Example 1

A mixture was prepared by sufficiently mixing 22% by mass MEA, 43% by mass mPDMS, 25% by mass DMAA, 10% by mass 164B, 0.5% by mass NB, 0.02% by mass RB, 0.2% by mass IC, and 40% by mass TAA together, and the mixture was filtered through a membrane filter (0.45 μm) to remove insoluble components, to obtain a monomer composition. Here, the total of MEA, mPDMS, DMA, and 164B, which form a silicone hydrogel after polymerization, is regarded as 100% by mass in the calculation. The monomer composition was injected into a contact lens mold made of a transparent resin (base curve side, polypropylene; front curve side, cyclic polyolefin), and irradiated with light (1.01 mW/cm$^2$, 20 minutes) using a fluorescent lamp (Toshiba, FL-6D, daylight color, 6 W, four tubes) under a nitrogen atmosphere to allow polymerization. After the polymerization, the composition, together with the mold, was immersed in a solution of isopropyl alcohol:water=1:1, and warmed at 60° C. for 1 hour, followed by detaching a molded article having a contact lens shape from the mold. The resulting molded article was immersed in a solution of isopropyl alcohol:water=3:7 (volume ratio before mixing) at room temperature for 30 minutes, and then immersed in clean RO water. The article was then left to stand and stored overnight.

The molded article was taken out of the RO water, and then immersed in 1% by mass aqueous polyacrylic acid solution (weight average molecular weight, 250 kD) at room temperature for 10 minutes, followed by sufficient washing with RO water. Thereafter, the molded article was immersed in borate buffer, and then subjected to steam sterilization to prepare a contact lens sample. The resulting contact lens sample was subjected to various kinds of measurement. The results are summarized in Table 2.

Examples 2 to 6

Lenses were prepared in the same manner as in Example 1 except that the monomer mixing ratio was changed as shown in Table 1, and subjected to evaluation. The measurement results are summarized in Table 2.

Table 2 shows the results of measurement of various physical properties required for contact lenses. All of Examples 1 to 6 showed results sufficient for use as contact lenses.

Comparative Example 1

With reference to Patent Document 1, a monomer composition composed of 74.1% by mass MEA, 24.7% by mass TRIS, 1% by mass 3G, 0.2% by mass IC, and 45% by mass TAA was polymerized. However, the resulting product was just a white, strongly curled, and very sticky polymer mass, which was not suitable for use as a contact lens.

TABLE 1

| | | Comparative Example 1 | Example 1 | Example 2 | Example 3 | Example 4 | Example 5 | Example 6 |
|---|---|---|---|---|---|---|---|---|
| Monomer composition [% by mass] | MEA | 74.1 | 22 | 22 | | | 22 | 22 |
| | bm200 | | | | 22 | | | |
| | bm400 | | | | | 22 | | |
| | TRIS | 24.7 | | | | | | |
| | mPDMS | | 43 | 43 | 53 | 48 | | 43 |
| | FM0711 | | | | | | 43 | |
| | DMAA | | 25 | 25 | 15 | 20 | 25 | |
| | NVP | | | | | | | 25 |
| | 164A | | | | | 4 | | |
| | 164B | | 10 | | 10 | 6 | | 10 |
| | 164C | | | 10 | | | | |
| | FM7721 | | | | | | 10 | |
| | 3G | 1 | | | | | | |
| | NB | | 0.5 | 0.5 | 0.5 | 0.5 | 0.5 | 0.5 |
| | RB | | 0.02 | 0.02 | 0.02 | 0.02 | 0.02 | 0.02 |
| | IC | 0.2 | 0.2 | 0.2 | 0.2 | 0.2 | 0.2 | 0.2 |
| | TAA | 45 | 40 | 40 | 40 | 40 | 40 | 40 |
| Silicon atom content in dry state [%] | | 6.6 | 16.6 | 16.7 | 19.7 | 18.1 | 17.1 | 16.6 |

TABLE 2

| | | Comparative Example 1 | Example 1 | Example 2 | Example 3 | Example 4 | Example 5 | Example 6 |
|---|---|---|---|---|---|---|---|---|
| In hydrous state | Diameter (mm) | N/A$^\alpha$ | 14.6 | 14.8 | 14.3 | 14.7 | 14.8 | 14.7 |
| | Transparency | 1 | 4 | 4 | 4 | 5 | 4 | 4 |
| | Wettability (seconds) | 0 | 60<$^\beta$ | 60<$^\beta$ | 60<$^\beta$ | 48.6 | 60<$^\beta$ | 60<$^\beta$ |
| | Water content (%) | 26.9 | 31.7 | 35.0 | 30.1 | 35.9 | 33.3 | 32.1 |
| | Tensile elongation (%) | N/A$^\alpha$ | 464 | 537 | 217 | 291 | 509 | 369 |
| | Elastic modulus (MPa) | N/A$^\alpha$ | 0.57 | 0.43 | 0.53 | 0.61 | 0.48 | 0.45 |
| | Zero-stress period (seconds) | N/A$^\alpha$ | <1$^\gamma$ | <1$^\gamma$ | <1$^\gamma$ | <1$^\gamma$ | <1$^\gamma$ | <1$^\gamma$ |
| | Lubrication | N/A$^\alpha$ | 5 | 5 | 5 | 5 | 5 | 5 |
| | Dynamic contact angle, advancing (°) | N/A$^\alpha$ | 33.2 | 34.7 | 34.1 | 33.3 | 34.3 | 34.8 |
| | Dynamic contact angle, receding (°) | N/A$^\alpha$ | 32.0 | 32.0 | 31.8 | 27.6 | 32.1 | 31.2 |

Examples 8 to 13

The components described in Table 3 were mixed well, and the resulting mixture was filtered through a membrane filter (0.45 μm) to remove insoluble components, to obtain a monomer composition. The monomer composition was injected into a contact lens mold made of a resin (polypropylene). Under air atmosphere, irradiation was performed using an LED light with a center wavelength of 405 nm at 0.8 mW/cm$^2$ for 1 hour from above and below the monomer composition, to allow polymerization. After the polymerization, the composition, together with the mold, was immersed in a solution of isopropyl alcohol:water=7:3 (volume ratio before mixing), and warmed at 70° C. for 1 hour, followed by detaching a molded article having a contact lens shape from the mold. The resulting molded article was immersed in a solution of isopropyl alcohol:water=7:3 (volume ratio before mixing) at 70° C. for 3 hours, and then immersed in clean RO water. The article was then left to stand and stored overnight. The molded article was taken out of the RO water, and then immersed in 1% by mass aqueous polyacrylic acid solution (weight average molecular weight, 250 kD) at room temperature for 10 minutes, followed by sufficient washing with RO water. Thereafter, the molded article was immersed in borate buffer, and then subjected to steam sterilization to prepare a contact lens. The resulting contact lens was subjected to various kinds of measurement. The results are summarized in Table 4.

TABLE 3

| | | Example 8 | Example 9 | Example 10 | Example 11 | Example 12 | Example 13 | Example 14 |
|---|---|---|---|---|---|---|---|---|
| Monomer composition [% by mass] | MEA | 22 | 22 | 22 | 22 | 22 | 22 | 22 |
| | mPDMS | | | | | 40 | 43 | 23 |
| | FM0711 | 40 | 40 | 40 | 40 | | | |
| | DMAA | 25 | 25 | 25 | 25 | 25 | 25 | 45 |
| | 164AS | 10 | 8 | 6 | 4 | 10 | | |
| | 164A | | | | | | 10 | 10 |
| | NB | 0.5 | 0.5 | 0.5 | 0.5 | 0.5 | 0.5 | 0.1 |
| | RB | 0.02 | 0.02 | 0.02 | 0.02 | 0.02 | 0.02 | 0.1 |
| | IC | 0.5 | 0.5 | 0.5 | 0.5 | 0.5 | 0.2 | 0.2 |
| | TAA | 40 | 40 | 40 | 40 | 40 | 40 | 40 |
| Silicon atom content in dry state [%] | | 15.8 | 15.5 | 15.3 | 15.0 | 15.5 | 16.4 | 10.3 |

Example 14

Contact lenses were prepared in the same manner as in Examples 8 to 13 except that polymerization was carried out by irradiation using a fluorescent lamp (Toshiba, FL-6D, daylight color, 6 W, four tubes) (1.01 mW/cm$^2$, 20 minutes). Results of various kinds of measurement are shown in Table 4.

Example 7, Examples 15 to 21, and Comparative Examples 2 to 4 (Comparison with Commercially Available Products)

The following three kinds of commercially available products, and the lenses of Example 1 and Examples 8 to 14, were compared for the physical properties shown in Table 4 (wherein the oxygen permeability values for "Dailies Total 1" (registered trademark) and "MyDay" (registered trademark) in Table 4 were calculated from values available from the manufacturers).

Oasys: "ACUVUE" (registered trademark), manufactured by Johnson & Johnson Total one: "Dailies Total 1" (registered trademark), manufactured by Alcon MyDay: "MyDay" (registered trademark), manufactured by CooperVision Here, the results of evaluation of physical properties using the lens of Example 1 are shown as Example 7; the results of evaluation of physical properties using the lenses of Examples 8 to 14 are shown as Examples 15 to 21; and the results for Oasys, Total one, and MyDay are shown as Comparative Example 2, Comparative Example 3, and Comparative Example 4, respectively, in Table 4.

TABLE 4

| | | | | In hydrous state | | | | In dry state | |
|---|---|---|---|---|---|---|---|---|---|
| | | Transparency | Wettability (seconds) | Water content (%) | Tensile elongation at break (%) | Tensile Elastic Modulus (MPa) | Oxygen permeability coefficient (*) | Tensile Elastic Modulus (MPa) | Dry elastic modulus ratio |
| Comparative Example 2 | Oasys | 3 | 12.8 | 36.2 | 367 | 0.8 | 83 | 15 | 18.8 |
| Comparative Example 3 | Total one | 4 | 60<$^\beta$ | 30.5 | 255 | 0.7 | 105 | 9.1 | 12.8 |
| Comparative Example 4 | MyDay | 4 | 60<$^\beta$ | 55.0 | 388 | 0.5 | 60 | 16 | 29.6 |
| Example 7 | Lens of Example 1 | 4 | 60<$^\beta$ | 31.7 | 464 | 0.6 | 80 | 1.3 | 2.2 |
| Example 15 | Lens of Example 8 | 4 | 60<$^\beta$ | 34.6 | — | 1.1 | — | 1.8 | 1.5 |
| Example 16 | Lens of Example 9 | 4 | 60<$^\beta$ | 32.7 | — | 0.9 | — | 1.7 | 1.9 |
| Example 17 | Lens of Example 10 | 4 | 60<$^\beta$ | 30.8 | — | 0.9 | — | 1.7 | 1.9 |
| Example 18 | Lens of Example 11 | 4 | 60<$^\beta$ | 33.0 | — | 0.6 | — | 1.7 | 3.0 |
| Example 19 | Lens of Example 12 | 4 | 60<$^\beta$ | 32.4 | — | 0.8 | — | 1.5 | 1.8 |
| Example 20 | Lens of Example 13 | 4 | 60<$^\beta$ | 33.6 | — | 0.8 | — | 0.8 | 1.0 |
| Example 21 | Lens of Example 14 | 4 | 60<$^\beta$ | 40.3 | — | 0.6 | — | 2.4 | 4.2 |

Regarding the tensile elastic modulus in dry state, the commercially available products showed values of not less than 9 MPa, indicating very high hardness. In contrast, the lenses of Example 1 and Examples 8 to 14 of the present invention showed values of as low as about 0.8 to 2.4 MPa even in dry state, indicating softness of these lenses equivalent to that in hydrous state.

From these results, it can be said that the silicone hydrogel lens used in the present invention has an appropriate tensile elastic modulus in hydrous state, and excellent oxygen permeability, transparency, and shape recovery performance, that these physical properties are satisfied in a well-balanced manner, and that the lens has a sufficiently low tensile elastic modulus in either hydrous state or dry state, so that the lens allows suppression of stimulation of the eyeball due to dryness.

The meanings of the symbols used in the tables are as follows.
- α: "N/A" means that measurement was impossible.
- β: "60<" means an excellent wettability of not less than 60 seconds.
- γ: "<1" means an excellent shape recovery performance of 0.1 second to 1 second.
- The unit of the oxygen permeability coefficient (*) is as follows: $\times 10^{-11}$: $(cm^2/second)\ mL\ O_2/(mL \cdot hPa)$.

Example 22

Instead of the contact lens mold made of a transparent resin used in Example 1, two transparent glass plates having a size of 10 cm×10 cm with a thickness of 3 mm and a spacer with a thickness of 200 μm sandwiched therebetween were used.

The spacer was prepared by stacking two sheets each of which was prepared by cutting out the central portion (a square of 6 cm×6 cm) of "Parafilm" (registered trademark; LMS Co., Ltd.) having a size of 10 cm×10 cm×100-μm thickness. A film-shaped molded article was obtained by the same procedure as in Example 1 except that the monomer composition was filled into the gap formed with the glass plates and the spacer instead of the contact lens mold made of a transparent resin. An area of 3 cm×3 cm near the center of the resulting film-shaped molded article was cut out. The resulting piece was applied to the skin. As a result, it was flexible and gave a good feeling of touch. The good feeling of touch continued even in dry state since hardening of the article did not occur. It was thus thought that the article can be suitably used as a wound dressing.

Example 23

With reference to JP 6-510687 A, a corneal inlay having a diameter of 2 mm, central thickness of 20 μm, peripheral thickness of 20 μm, base radius of curvature of 7.6 mm, and optical power of +2.5 D was prepared. The corneal inlay was obtained by the same procedure as in Example 1 except that a corneal inlay mold made of a transparent resin was used instead of the contact lens mold made of a transparent resin. It was thought that the resulting product can be suitably used as a corneal inlay.

INDUSTRIAL APPLICABILITY

Examples of uses of the present invention include ophthalmic lenses, endoscopes, catheters, infusion tubes, gas transfer tubes, stents, sheaths, cuffs, tube connectors, access ports, drainage bags, blood circuits, wound dressings, and drug carriers. In particular, contact lenses, intraocular lenses, artificial corneas, corneal inlays, and corneal onlays are preferred. Contact lenses are most preferred.

The invention claimed is:

1. A medical device comprising a silicone hydrogel satisfying the following conditions:
   (1) a water content in hydrous state which is within the range of 20% by mass to 70% by mass;
   (2) a content of silicon atoms with respect to the total mass in dry state which is within the range of 8% by mass to 30% by mass; and
   (3) a tensile elastic modulus in dry state which is within the range of 0.1 MPa to 3.5 MPa;
   wherein the silicone hydrogel is a polymer comprising:
   a repeat unit (A) in an amount within the range of 5% by mass to 50% by mass with respect to the total mass of the silicone hydrogel in dry state, the repeat unit (A) being derived from a monomer represented by General Formula (I):

$$\underset{O}{\overset{R^a}{\underset{\|}{\diagup\!\!\!\!\diagdown}}}\!\!-\!\!O\!-\!(CH_2\!-\!CH_2\!-\!O)_n\!-\!R^b \quad (I)$$

wherein, in General Formula (I), $R^a$ represents hydrogen or a methyl group; $R^b$ represents an alkyl group having from 1 to 15 carbon atoms; and n represents an integer within the range of 1 to 40;

a repeat unit (B) in an amount within the range of 20% by mass to 70% by mass with respect to the total mass of the silicone hydrogel in dry state, the repeat unit (B) being derived from a monomer represented by General Formula (a):

$$\underset{O}{\overset{R^1}{\underset{\|}{\diagup\!\!\!\!\diagdown}}}\!\!-\!\!O\!-\!R^2\!-\!\underset{R^4}{\overset{R^3}{\underset{|}{Si}}}\!-\!\left(O\!-\!\underset{R^6}{\overset{R^5}{\underset{|}{Si}}}\right)_k\!\!-\!R^7 \quad (a)$$

wherein, in General Formula (a), $R^1$ represents a hydrogen atom or a methyl group; $R^2$ represents a propylene group; $R^3$ to $R^6$ each independently represent a $C_1$-$C_4$ alkyl group; $R^7$ represents a $C_1$-$C_6$ alkyl group which is optionally substituted; and k represents an integer of 1 to 200 which optionally has a distribution; and a repeat unit (C) in an amount within the range of 5% by mass to 50% by mass with respect to the total mass of the silicone hydrogel in dry state, the repeat unit (C) being derived from a monomer represented by General Formula (II-1):

$$\underset{O}{\overset{R^8}{\underset{\|}{\diagup\!\!\!\!\diagdown}}}\!\!\underset{}{\overset{R^9}{\underset{|}{N}}}\!\!-\!R^{10} \quad (II\text{-}1)$$

or General Formula (II-2):

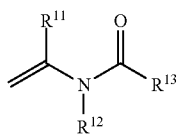

(II-2)

wherein, in General Formula (II-1) and General Formula (II-2), $R^8$ and $R^{11}$ each independently represent a hydrogen atom or a methyl group; $R^9$ and $R^{10}$, and $R^{12}$ and $R^{13}$ represent a hydrogen atom(s), and/or a $C_1$-$C_{20}$ alkyl group(s) which is/are either branched or linear, which optionally contain(s) a cyclic structure, and which is/are optionally substituted; and $R^{12}$ and $R^{13}$ optionally bind to each other to form a ring;

with the proviso that the total of the repeat units (A), (B), and (C) does not exceed 100% by mass with respect to the total mass of the silicone hydrogel in dry state; and wherein the total of the repeat units (A), (B), and (C) exceeds 50% by mass with respect to the total mass of the silicone hydrogel in dry state.

2. The medical device according to claim 1, wherein the tensile elastic modulus is within the range of 0.1 MPa to 1.5 MPa.

3. The medical device according to claim 1, comprising a silicone hydrogel having a dry elastic modulus ratio of 0.1 to 10, wherein the dry elastic modulus ratio is represented by the following Equation 1:

dry elastic modulus ratio=the tensile elastic modulus in dry state/tensile elastic modulus in hydrous state (1).

4. The medical device according to claim 1, wherein the silicone hydrogel has a zero-stress period of 0.1 second to 2 seconds in hydrous state, wherein the zero-stress period means a length of time during tensile stress measurement in which an operation of drawing a test piece having a width of 5 mm and a thickness within the range of 0.05 mm to 0.2 mm held at an inter-supporting-point distance of 5 mm, using a load cell with a maximum load of 2 kg at a rate of 100 mm/minute, until the inter-supporting-point distance becomes 10 mm, and then reducing the inter-supporting-point distance to 5 mm at the same rate, is repeated three times while obtaining measured values at 20-millisecond intervals, the length of time being a length of time from the time point when the stress becomes zero during the second reduction of the inter-supporting-point distance to 5 mm to the time point when the stress becomes non-zero after starting the third drawing, wherein zero stress means a state with a measured value within the range of −0.05 gf to 0.05 gf.

5. The medical device according to claim 1, wherein the silicone hydrogel has a tensile elongation at break within the range of 200% to 1000% in hydrous state.

6. The medical device according to claim 3, wherein the silicone hydrogel has a tensile elastic modulus within the range of 0.1 MPa to 1.5 MPa in hydrous state.

7. The medical device according to claim 1, wherein the repeat unit (C) derived from a monomer containing an amide structure has a glass transition temperature of not more than 20° C. in a state of a homopolymer.

8. The medical device according to claim 1, which is any one selected from the group consisting of ophthalmic lenses, endoscopes, catheters, infusion tubes, gas transfer tubes, stents, sheaths, cuffs, tube connectors, access ports, drainage bags, blood circuits, wound dressings, and drug carriers.

9. The medical device according to claim 1, which is a contact lens.

* * * * *